United States Patent
Park et al.

(10) Patent No.: US 9,302,903 B2
(45) Date of Patent: Apr. 5, 2016

(54) MICRONEEDLE DEVICES AND PRODUCTION THEREOF

(75) Inventors: Jung-Hwan Park, Atlanta, GA (US); Mark R. Prausnitz, Decatur, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 365 days.

(21) Appl. No.: 10/023,259

(22) Filed: Dec. 14, 2001

(65) Prior Publication Data

US 2002/0082543 A1    Jun. 27, 2002

Related U.S. Application Data

(60) Provisional application No. 60/255,603, filed on Dec. 14, 2000.

(51) Int. Cl.
*A61N 1/30* (2006.01)
*B81C 1/00* (2006.01)
(Continued)

(52) U.S. Cl.
CPC .......... *B81C 1/00111* (2013.01); *A61B 5/1411* (2013.01); *A61B 5/14514* (2013.01); *A61M 37/0015* (2013.01); *A61N 1/30* (2013.01);
(Continued)

(58) Field of Classification Search
CPC .................. A61M 37/0015; A61M 2037/0023; A61M 2037/0007; A61M 2037/003
USPC ............... 604/20, 21, 46, 181, 171, 173, 183, 604/184, 191, 239, 258, 272, 500, 506, 507, 604/273, 264; 128/898; 424/449, 483; 427/2.1, 2.13
See application file for complete search history.

(56) References Cited

U.S. PATENT DOCUMENTS

| 1,274,081 A | 7/1918 | Riethmueller |
| 2,559,474 A | 7/1951 | Son |

(Continued)

FOREIGN PATENT DOCUMENTS

| DE | 195 25 607 | 1/1997 |
| EP | 0497620 | 5/1992 |

(Continued)

OTHER PUBLICATIONS

Abrams, S.B. Versatile biosensor is compact and cheap. Biophotonics International 32-34 (Jan./Feb. 1998).
(Continued)

*Primary Examiner* — Phillip Gray
(74) *Attorney, Agent, or Firm* — King & Spalding

(57) ABSTRACT

Microneedle devices and methods of manufacture are provided for transport of molecules or energy across or into biological barriers, such as skin. The device can comprise one or more microneedles formed of a first material and a second material, wherein the second material is dispersed throughout the first material or forms a portion of the microneedle. The first material preferably is a polymer. The second material can be pore forming agents, structural components, biosensor, or molecules for release, such as drug. The device also can comprise a substrate and a plurality of microneedles extending from the substrate, wherein the microneedles have a beveled or tapered tip portion, a longitudinally extending exterior channel, or both. Methods of making these devices include providing a mold having a plurality of microdepressions which define the surface of a microneedle; filling the microdepressions with a first molding material; and molding the material, thereby forming microneedles.

36 Claims, 12 Drawing Sheets

(51) Int. Cl.
  *A61B 5/15* (2006.01)
  *A61M 37/00* (2006.01)
  *A61B 5/145* (2006.01)

(52) U.S. Cl.
  CPC .. *A61M2037/003* (2013.01); *A61M 2037/0053* (2013.01); *B81B 2201/055* (2013.01)

(56) References Cited

U.S. PATENT DOCUMENTS

| | | | |
|---|---|---|---|
| 2,814,296 A | 11/1957 | Everett | |
| 2,893,392 A | 7/1959 | Wagner | |
| 3,034,507 A | 5/1962 | McConnell et al. | |
| 3,072,122 A | 1/1963 | Rosenthal | |
| 3,086,530 A | 4/1963 | Groom | |
| 3,123,212 A | 3/1964 | Taylor et al. | |
| 3,136,314 A | 6/1964 | Kravitz | |
| RE25,637 E | 9/1964 | Kravitz et al. | |
| 3,221,739 A | 12/1965 | Rosenthal | |
| 3,221,740 A | 12/1965 | Rosenthal | |
| 3,556,080 A | 1/1971 | Hein | |
| 3,583,399 A | 6/1971 | Ritsky | |
| 3,595,231 A | 7/1971 | Pistor | |
| 3,596,660 A | 8/1971 | Melone | |
| 3,675,766 A | 7/1972 | Rosenthal | |
| 3,762,307 A | 10/1973 | Badovinac | |
| 3,918,449 A | 11/1975 | Pistor | |
| 3,964,482 A * | 6/1976 | Gerstel | A61K 9/0021 424/449 |
| 4,109,655 A | 8/1978 | Chacornac | |
| 4,159,659 A | 7/1979 | Nightingale | |
| 4,182,002 A | 1/1980 | Holec | |
| 4,222,392 A | 9/1980 | Brennan | |
| 4,320,758 A | 3/1982 | Eckenhoff et al. | |
| 4,411,657 A | 10/1983 | Galindo | |
| 4,494,950 A | 1/1985 | Fischell | |
| 4,512,768 A | 4/1985 | Rangaswamy | |
| 4,653,513 A | 3/1987 | Dombrowski | |
| 4,664,651 A | 5/1987 | Weinshenker et al. | |
| 4,671,288 A | 6/1987 | Gough | |
| 4,703,761 A | 11/1987 | Rathbone et al. | |
| 4,771,660 A | 9/1988 | Yacowitz | |
| 4,775,361 A | 10/1988 | Jacques et al. | |
| 4,798,582 A | 1/1989 | Sarath et al. | |
| 4,830,217 A | 5/1989 | Dufresne et al. | |
| 4,837,049 A | 6/1989 | Byers et al. | |
| 4,886,499 A | 12/1989 | Cirelli et al. | |
| 4,921,475 A | 5/1990 | Sibalis | |
| 4,969,468 A | 11/1990 | Byers et al. | |
| 5,035,711 A | 7/1991 | Aoki et al. | |
| 5,054,339 A | 10/1991 | Yacowitz | |
| 5,138,220 A | 8/1992 | Kirkpatrick | |
| 5,147,355 A | 9/1992 | Friedman et al. | |
| 5,241,969 A | 9/1993 | Carson et al. | |
| 5,250,023 A | 10/1993 | Lee et al. | |
| 5,257,987 A | 11/1993 | Athayde et al. | |
| 5,279,544 A | 1/1994 | Gross et al. | |
| 5,279,552 A | 1/1994 | Magnet | |
| 5,335,670 A | 8/1994 | Fishman | |
| 5,364,374 A | 11/1994 | Morrison et al. | |
| 5,383,512 A | 1/1995 | Jarvis | |
| 5,396,897 A | 3/1995 | Jain et al. | |
| 5,401,242 A | 3/1995 | Yacowitz | |
| 5,451,210 A | 9/1995 | Kramer et al. | |
| 5,457,041 A | 10/1995 | Ginaven et al. | |
| 5,527,288 A | 6/1996 | Gross et al. | |
| 5,582,184 A | 12/1996 | Erickson et al. | |
| 5,591,139 A | 1/1997 | Lin et al. | |
| 5,599,302 A | 2/1997 | Lilley et al. | |
| 5,605,662 A | 2/1997 | Heller et al. | |
| 5,611,806 A | 3/1997 | Jang | |
| 5,611,809 A | 3/1997 | Marshall et al. | |
| 5,611,942 A | 3/1997 | Mitsui et al. | |
| 5,618,295 A | 4/1997 | Min | |
| 5,632,730 A | 5/1997 | Reinert | |
| 5,632,957 A | 5/1997 | Heller et al. | |
| 5,647,851 A | 7/1997 | Pokras | |
| 5,658,515 A | 8/1997 | Lee et al. | |
| 5,662,619 A | 9/1997 | Zarate | |
| 5,680,858 A | 10/1997 | Hansen et al. | |
| 5,697,901 A | 12/1997 | Eriksson | |
| 5,722,397 A | 3/1998 | Eppstein | |
| 5,725,494 A | 3/1998 | Brisken et al. | |
| 5,758,505 A | 6/1998 | Dobak et al. | |
| 5,801,057 A | 9/1998 | Smart et al. | |
| 5,807,375 A | 9/1998 | Gross et al. | |
| 5,843,114 A | 12/1998 | Jang | |
| 5,848,991 A | 12/1998 | Gross et al. | |
| 5,852,495 A | 12/1998 | Parce | |
| 5,855,801 A | 1/1999 | Lin et al. | |
| 5,858,188 A | 1/1999 | Soane et al. | |
| 5,865,786 A | 2/1999 | Sibalis et al. | |
| 5,865,796 A | 2/1999 | McCabe | |
| 5,876,675 A | 3/1999 | Kennedy | |
| 5,879,326 A | 3/1999 | Allen et al. | |
| 5,883,211 A | 3/1999 | Sassi et al. | |
| 5,885,211 A | 3/1999 | Eppstein et al. | |
| 5,899,880 A | 5/1999 | Bellhouse et al. | |
| 5,911,223 A | 6/1999 | Weaver et al. | |
| 5,919,159 A | 7/1999 | Lilley et al. | |
| 6,050,988 A | 4/2000 | Zuck | |
| 6,080,116 A | 6/2000 | Erickson et al. | |
| 6,132,755 A * | 10/2000 | Eicher | A61M 31/002 424/427 |
| 6,155,992 A | 12/2000 | Henning | |
| 6,219,574 B1 | 4/2001 | Cormier et al. | |
| 6,312,612 B1 | 11/2001 | Sherman et al. | |
| 6,334,856 B1* | 1/2002 | Allen et al. | 604/191 |
| 6,440,096 B1 | 8/2002 | Lastovich et al. | |
| 6,503,231 B1 | 1/2003 | Prausnitz et al. | |
| 6,527,778 B2 | 3/2003 | Athanasiou et al. | |
| 6,532,386 B2* | 3/2003 | Sun | A61M 37/0015 604/20 |
| 6,537,242 B1 | 3/2003 | Palmer | |
| 6,551,622 B1 | 4/2003 | Jackson | |
| 6,595,947 B1* | 7/2003 | Mikszta | A61B 17/205 604/27 |
| 6,611,707 B1 | 8/2003 | Prausnitz et al. | |
| 6,623,457 B1 | 9/2003 | Rosenberg | |
| 6,669,663 B1 | 12/2003 | Thompson | |
| 6,689,103 B1 | 2/2004 | Palasis | |
| 6,743,211 B1 | 6/2004 | Prausnitz et al. | |
| 7,226,439 B2 | 6/2007 | Prausnitz et al. | |
| 7,344,499 B1 | 3/2008 | Prausnitz et al. | |
| 2001/0053891 A1 | 12/2001 | Ackley | |
| 2002/0133129 A1* | 9/2002 | Arias et al. | 604/272 |
| 2004/0049150 A1* | 3/2004 | Dalton et al. | 604/46 |
| 2005/0065463 A1 | 3/2005 | Tobinaga et al. | |
| 2005/0137531 A1 | 6/2005 | Prausnitz et al. | |
| 2005/0197308 A1* | 9/2005 | Dalton et al. | 514/44 |
| 2006/0036209 A1 | 2/2006 | Subramony et al. | |
| 2007/0225676 A1 | 9/2007 | Prausnitz et al. | |
| 2007/0293814 A1 | 12/2007 | Trautman et al. | |
| 2008/0027384 A1 | 1/2008 | Wang et al. | |
| 2008/0058706 A1 | 3/2008 | Zhang et al. | |
| 2008/0161747 A1 | 7/2008 | Lee et al. | |
| 2008/0319298 A1 | 12/2008 | Huys et al. | |
| 2009/0062767 A1 | 3/2009 | Van Antwerp et al. | |
| 2009/0131905 A1 | 5/2009 | Allen et al. | |
| 2009/0208140 A1 | 8/2009 | Jayant et al. | |
| 2009/0232203 A1 | 9/2009 | Jayant et al. | |

FOREIGN PATENT DOCUMENTS

| | | |
|---|---|---|
| EP | 0652600 | 5/1995 |
| JP | 7132119 | 5/1995 |
| JP | 7196314 | 8/1995 |
| WO | WO 93/17754 | 9/1993 |
| WO | WO 96/37256 | 11/1996 |
| WO | WO 96/40365 | 12/1996 |
| WO | WO 96/41236 | 12/1996 |
| WO | WO 97/07734 | 3/1997 |
| WO | WO 98/00193 | 1/1998 |
| WO | WO 98/00194 | 1/1998 |

(56) References Cited

FOREIGN PATENT DOCUMENTS

| WO | WO 98/28037 | 7/1998 |
|---|---|---|
| WO | WO-99/64580 | 12/1999 |
| WO | WO 00/35530 | 6/2000 |
| WO | WO 00/48669 | 8/2000 |
| WO | WO 00/74763 | 12/2000 |

OTHER PUBLICATIONS

Amsden, B.G. and Goosen, M.F.A. Transdermal Delivery of Peptide and Protein Drugs: an Overview. AlChE J. 41, 1972-1977 (Aug. 1995).

Brumlik, C.J. and Martin, C.R. Template Synthesis of Metal Microtubules. J. Am. Chem. Soc. 113, 3174-3175 (1991).

Chun, K. et al. Fabrication of Array of Hollow Microcapillaries Used for Injection of Genetic Materials into Animal/Plant Cells. Jpn. J. Appl. Phys. 38, 279-281 (1999).

Clarke, M.S.F. and McNeil, P.L. Syringe loading introduces macromolecules into living mammalian cell cytosol. J. Cell. Sci. 102, 533-541 (1992).

Despont, M. et al. High-Aspect-Ratio, Ultrathick, Negative-Tone Near-UV Photoresist for Mems Applications. IEEE 0-7803-3744-1/97 (1997).

Edell, D.J. et al. Factors Influencing the Biocompatibility of Insertable Silicon Microshafts in Cerebral Cortex. IEEE Transactions on Biomedical Engineering 39, 635-643 (1992).

Eleventh Annual International Workshop on Micro Electro Mechanical Systems, Heidelberg, Germany (Jan. 25-29, 1998). IEEE Catalog No. 98CH36176.

Frazier, A.B. and Allen, M.G. Metallic Microstructures Fabricated Using Photosensitive Polymide Electroplating Molds. J. Microelectromechanical Systems 2, 87-94 (Jun. 1993).

Frazier, A.B. et al. Two Dimensional Metallic Microelectrode Arrays for Extracellular Stimulation and Recording of Neurons. IEEE 0-7803-0957 pp. 195-200 (Feb. 1993).

Griss, P. et al. Micromachined Electrodes for Biopotential Measurements. J. Microelectromechanical Systems 10, 10-16 (Mar. 2001).

Haga et al. Transdermal Iontophoretic delivery of insulin using a photoetched microdevice. J. Controlled Release 43, 139-149 (1997).

Hashmi, S. et al. Genetic Transformation of Nematodes Using Arrays of Micromechanical Piercing Structures. BioTechniques 19, 766-770 (Nov. 1995).

Henry, S. et al. Micromachined Needles: A Novel Approach to Transdermal Drug Delivery. J. Pharm. Sci. 87, 922-925 (Aug. 1998).

Henry et al. Microfabricated Microneedles: A Novel Method to Increase Transdermal Drug Delivery. J. Pharm. Sci. 87, 922-925 (1998).

Hoffert, S.P. Transcutaneous Methods Get Under the Skin. The Scientist 12, No. 16 (Aug. 17, 1998).

Infiltrator Intramural Drug Delivery: A New Generation of Drug Delivery Catheters from InterVentional Technologies, Inc., San Diego, CA (1997).

Jaeger, R.C. *Introduction to Microelectronic Fabrication* in the Addison-Wesley Modular Series on Solid State Devices, G.W. Neudeck and R.F. Pierret, eds. vol. 5, Addison-Wesley Publishing Co., Inc. (May 1993).

Jansen, H. et al. The Black Silicon Method IV: The Fabrication of Three-Dimensional Structures in Silicon with High Aspect Ratios for Scanning Probe Microscopy and Other Applications. MESA Res. Int, University of Twente, The Nethlerlands.

Laermer, F. et al. Bosch Deep Silicon Etching: Improving Uniformity and Etch Rate for Advanced MEMS Application. IEEE Catalog No. 99CH36291C, ISBN: 0-7803-5194-0 from the Twelfth IEEE International Conference on Micro Electro Mechanical Systems, Orlando FL, (Jan. 17, 1999).

Langer, R. Drug delivery and targeting. Nature 392 Supp, 5-10 (Apr. 30, 1998).

Lehmann, V. Porous Silicon—A New Material for MEMS. IEEE ISBN: 0-7803-2985-6/96 (1996).

Lin, L. et al. Silicon Processed Microneedles. The 7th International Conference on Solid-State Sensors and Actuators (1993).

Martin, C.R. et al. Template Synthesis of Organic Microtubules. J. Am. Chem. Soc. 112, 8976-8977 (1990).

Najafi, K. and Hetke, J.F. Strength Characterization of Silicon Microprobes in Neurophysiological Tissues. IEEE Transactions on Biomedical Engineering 37, 474-481 (May 1990).

101 Uses for Tiny Tubules. Science 247 (Mar. 23, 1990).

*Percutaneous Absorption*, R.L. Bronaugh and H.I. Maibach, eds. Marcel Dekker, Inc., New York (1989).

Prausnitz, M.R. Reversible Skin Permeabilization for Transdermal Delivery of Macromolecules. Critical Reviews in Therapeutic Drug Carrier Systems 14, 455-483 (1997).

Quan, M. Plasma etch yields microneedle arrays. Electronic Eng. Times, p. 63 (Jul. 13, 1996).

Reiss, S.M. Glucose- and Blood-Monitoring Systems Vie for Top Spot. Biophotonics International p. 43-46 (May/Jun. 1997).

Runyan, W.R. and Bean, K.E. *Semiconductor Integrated Circuit Processing Technology*, Addison-Wesley Publishing Co. (1990).

Schift, H. et al. Fabrication of replicated high precision insert elements for micro-optical bench arrangements. SPIE vol. 3513, p. 122-134 from SPIE Conference on Microelectronic Structures and MEMS for Optical Processing IV, Santa Clara (Sep. 1998).

Single-crystal whiskers. Biophotonics Int'l, p. 64 (Nov./Dec. 1996).

Talbot, N.H. and Pisano, A.P. Polymolding: Two Wafer Polysilicon Micromolding of Closed-Flow Passages for Microneedles and Microfluidic Devices. Solid-State Sensor and Actuator Workshop, Hilton Head Island, SC (Jun. 8-11, 1998).

*Transdermal Drug Delivery*, J. Hadgraft and R.H. Guy, eds. Marcel Dekker, Inc., New York.

Trimmer, W. et al. Injection of DNA into Plant and Animal Tissues with Micromechanical Piercing Structures. IEEE Catalog No. 95CH35754, ISBN: 0-7803-2503-6 from Micro Electro Mechanical Systems, Amsterdam p. 111-115 (1995).

Weber, L. et al. Micro molding—a powerful tool for the large scale production of precise microstructures. SPIE No. 0-8194-2277-0/96, vol. 2879, p. 156-167 (1996).

Zuska, P. Microtechnology Opens Doors to the Universe of Small Space. MD&DI (1997).

Chun et al., "An Array of Hollow Microcapillaries for the Controlled Injection of Genetic Materials Into Animal/Plant Cells," *IEEE*, 1999, pp. 406-411.

Chun et al., "DNA Injection into Plant Cell Conglomerates by Micromachined Hollow Microcapillary Arrays," The 10th International Conference on Solid-State Sensors and Actuators: Transducers '99, Jun. 7-10, 1999, pp. 44-47.

Proceedings of the IEEE Micro Electro Mechanical Systems Conference 1987-1998, Rai-Chadhoury ed., *Handbook of Microlithography, Micromachining & Microfabrication* (SPIE Optical Engineering Press), Bellingham, WA, 1997.

\* cited by examiner

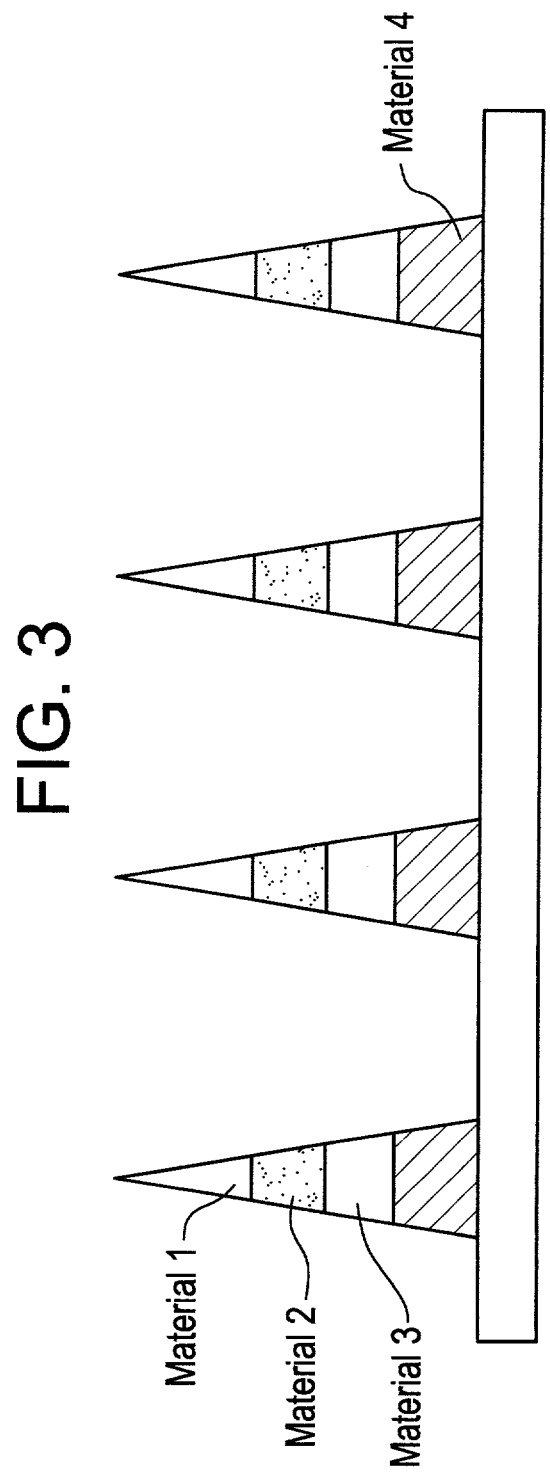

FIG. 6A
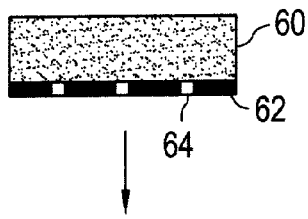
FIG. 6B  UV Exposure
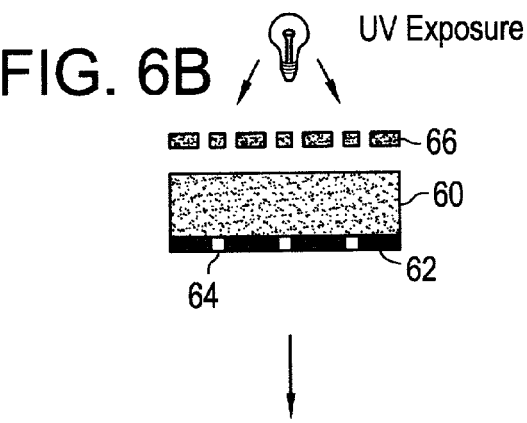
FIG. 6C
FIG. 6D
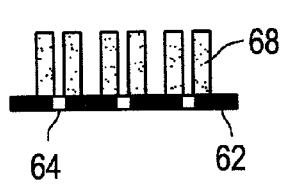
Developing of Non-X-linked SU-8
FIG. 6E
Silicone mold (Poly-dimethyl siloxane)
FIG. 6F
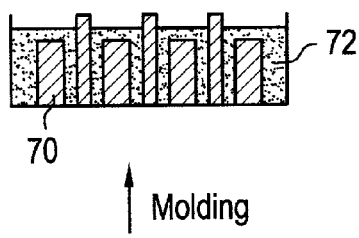
Molding
FIG. 6G
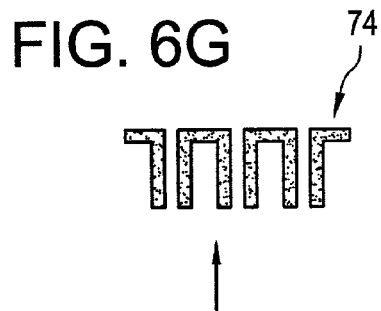

Developing of Non-X-linked SU-8

Metal Deposition

Filling up with SU-8

Molding

Silicone mold (Poly-dimethyl siloxane)

Developing

Reactive Ion Etching

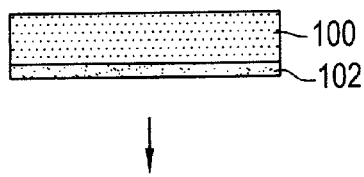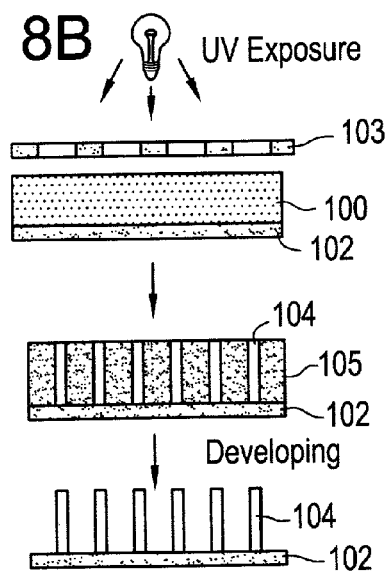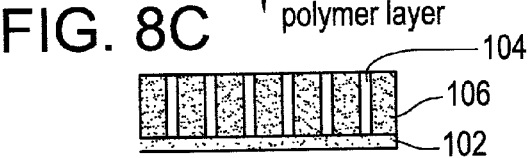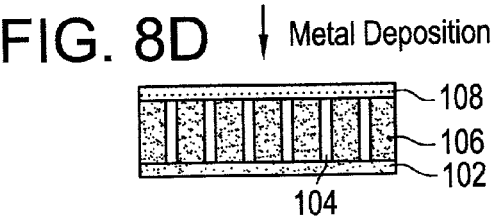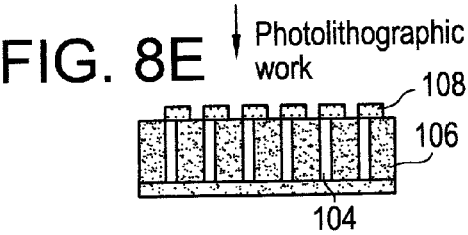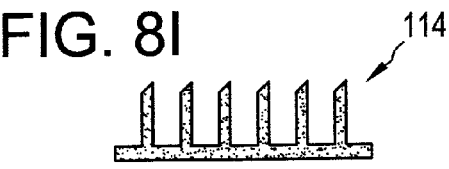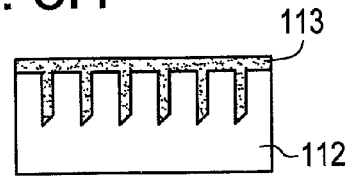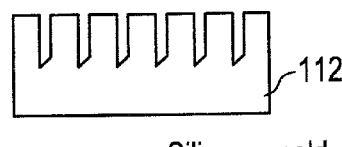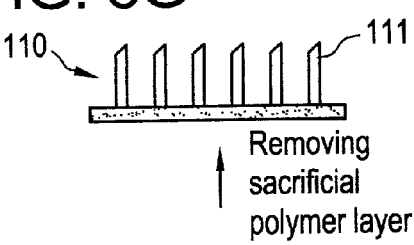

MICRONEEDLE DEVICES AND PRODUCTION THEREOF

CROSS-REFERENCE TO RELATED APPLICATIONS

Priority is claimed to U.S. provisional application No. 60/255,603, filed Dec. 14, 2000.

BACKGROUND OF THE INVENTION

This invention is generally in the field of devices for the controlled transport of molecules across tissue barriers, such as for drug delivery or sampling of biological fluids.

Numerous drugs and therapeutic agents have been developed in the battle against disease and illness. A frequent limitation to the effective and efficient use of these drugs, however, is their delivery, that is, how to transport the drugs across biological barriers in the body (e.g., the skin, the oral mucosa, the blood-brain barrier), which normally do not transport drugs at rates that are therapeutically useful or optimal.

Drugs are commonly administered orally as pills or capsules. Many drugs, however, cannot be effectively delivered in this manner, due to degradation in the gastrointestinal tract and/or elimination by the liver. Moreover, some drugs cannot effectively diffuse across the intestinal mucosa. Patient compliance may also be a problem, for example, in therapies requiring that pills be taken at particular intervals over a prolonged time.

Another common technique for delivering drugs across a biological barrier is the use of a conventional needle, such as those used with standard syringes or catheters, to transport drugs across (through) the skin. While effective for this purpose, needles generally cause pain, local damage to the skin at the site of insertion, bleeding, which increases the risk of disease transmission, and a wound sufficiently large to be a site of infection. Needle techniques also generally require administration by one trained in its use, and are undesirable for long-term, controlled continuous drug delivery.

Similarly, current methods of withdrawal or sampling bodily fluids, such as for diagnostic purposes, using a conventional needle are invasive and suffer from the same disadvantages. For example, needles or lancets are not preferred for frequent routine use, such as sampling of a diabetic's blood glucose or delivery of insulin, due to the vascular damage caused by repeated punctures. No alternative methodologies are currently in use. Proposed alternatives to the needle require the use of lasers or heat to create a hole in the skin, which is inconvenient, expensive, or undesirable for repeated use.

An alternative delivery technique is the transdermal patch, which usually relies on diffusion of the drug across the skin. However, this method is not useful for many drugs, due to the poor permeability (i.e. effective barrier properties) of the skin. The rate of diffusion depends in part on the size and hydrophilicity of the drug molecules and the concentration gradient across the stratum corneum. Few drugs have the necessary physiochemical properties to be effectively delivered through the skin by passive diffusion. Iontophoresis, electroporation, ultrasound, and heat (so-called active systems) have been used in an attempt to improve the rate of delivery. While providing varying degrees of enhancement, these techniques are not suitable for all types of drugs, failing to provide the desired level of delivery. In some cases, they are also painful and inconvenient or impractical for continuous controlled drug delivery over a period of hours or days.

Attempts have been made to design alternative devices for active transfer of drugs, or analyte to be measured, through the skin.

For example, U.S. Pat. No. 5,879,326 to Godshall et al. and PCT WO 96/37256 by Silicon Microdevices, Inc. disclose a transdermal drug delivery apparatus that includes a cutter portion having a plurality of microprotrusions, which have straight sidewalls, extending from a substrate that is in communication with a drug reservoir. In operation, the microprotrusions penetrate the skin until limited by a stop region of the substrate and then are moved parallel to the skin to create incisions. Channels in the substrate adjacent to the microprotrusions allow drug from the reservoir to flow to the skin near the area disrupted by the microprotrusions.

U.S. Pat. No. 5,250,023 to Lee et aL. discloses a transdermal drug delivery device, which includes a plurality of needles having a diameter in the range of 50 to 400 µm. The needles are supported in a water-swellable polymer substrate through which a drug solution permeates to contact the surface of the skin. An electric current is applied to the device to open the pathways created by the needles, following their withdrawal from the skin upon swelling of the polymer substrate.

PCT WO 93/17754 by Gross et al. discloses another transdermal drug delivery device that includes a housing having a liquid drug reservoir and a plurality of tubular elements for transporting liquid drug into the skin. The tubular elements may be in the form of hollow needles having inner diameters of less than 1 mm and an outer diameter of 1.0 mm.

While each of these devices has potential use, there remains a need for better drug delivery devices, which make smaller punctures or incisions, deliver drug with greater efficiency (greater drug delivery per quantity applied) and less variability of drug administration, and/or are easier to use. In view of these needs, microneedle devices have been developed, which are described in U.S. Ser. Nos. 09/095,221, filed Jun. 10, 1998, and 09/316,229, filed May 21, 1999, both by Prausnitz et al., and PCT WO 99/64580 and PCT WO 00/74763, which are hereby incorporated by reference. It would be advantageous, however, to provide additional methods of manufacturing devices having microneedles, particularly using materials and processes that are cost-effective and expand the range of useful properties and functions of the microneedles. It would also be useful to have biocompatible and biodegradable microneedles and increased ease of manufacture.

It is therefore an object of the present invention to provide an expanded selection of methods and materials for making and using microneedle devices for relatively painless, controlled and safe delivery or withdrawal of molecules across biological barriers such as skin.

It is a further object of the present invention to provide microneedle devices which can be produced inexpensively.

It is another object of the present invention to provide techniques for producing complex microneedle structures, yielding a variety of useful properties and functions of the microneedles.

SUMMARY OF THE INVENTION

Microneedle devices for transport of molecules, including drugs and biological molecules, across biological barriers, such as tissue or cell membranes, are provided, along with methods for their manufacture and use. In one embodiment, the device comprises one or more microneedles formed of a first material and a second material, wherein the second material is dispersed throughout the first material or forms a portion of the microneedle. The second material can be pore forming agents, structural components, biosensors, or molecules for release, such as drug (e.g., a vaccine). In another embodiment, the device comprises a substrate and a plurality of microneedles extending from the substrate, wherein the microneedles have a beveled or tapered tip portion, a longitudinally extending exterior channel, or both.

In a preferred embodiment, the microneedles are formed of a biocompatible and biodegradable polymer, such as polylactide, polyglycolide, and copolymers and blends thereof. The microneedles also can include, or be formed of, drug and/or additives or excipients. The polymer microneedles also can be fabricated to provide a microneedle having a defined porosity or having particles of reinforcing material distributed within the microneedle.

Methods for manufacturing these microneedle devices include micromolding, microfabrication, microshaping, and combinations thereof. In a preferred method, the steps include providing a mold having a plurality of microdepressions which define the surface of a microneedle; filling the microdepressions with a molding material; and molding the material, thereby forming microneedles. The molding methods are useful for forming microneedles from polymer, metals, and other materials. The methods enable the formation of microneedles having composite or layered structures which provide a control over the time and rate of release of drug or other agent and/or affect the mechanical properties of the microneedles. Porous microneedles can be formed by dispersing a leachable or volatilizable pore-forming agent in the microneedle material prior to forming the microneedles and then leaching or volatilizing the pore-forming agent from the microneedles.

In one embodiment, micromolds are filled with liquid monomer or a solution of monomer, the monomer is polymerized, and the polymer is directly or indirectly converted to a solid form in the shape of the microneedles. Alternatively, the micromold is filled with polymer powder, heated to melt the polymer, and then cooled to solidify the polymer in the shape of the microneedles. In another variation, the solid polymer can be exposed to carbon dioxide in amounts and under conditions effective to swell the polymer particles to form them together. The polymer powder also can be molded by compression molding. In a preferred embodiment, polymer melting is conducted under reduced pressure (e.g., vacuum conditions) in order to pull the polymer into the mold and displace any trapped gases, thereby minimizing or eliminating the formation of void defects in the microneedles. This approach overcomes the surface tension/wetting problems which can occur in large scale molding operations.

In another embodiment, the method comprises (i) forming one or more layers of a monomer or polymer material on a substrate; and (ii) selectively removing portions of the monomer or polymer material to form microneedles on the substrate. The monomer or polymer material on the substrate can comprise a first layer of a first material and a second layer of a second material, and can be crosslinkable. In the latter case, step (ii) can comprise using an optical mask to crosslink selected portions of the crosslinkable material; and then developing the uncrosslinked portions of the crosslinkable material, wherein the remaining crosslinked material forms the microneedles extending from the substrate. The optical mask can comprise a filled circle having one or more notches therein, effective to form a microneedle having a longitudinally extending exterior channel. The optical etch mask also can comprise a donut shape, effective to form a hollow microneedle or microneedle having a closed bore.

In variations of this method, step (ii) can further comprise (a) applying a sacrificial polymer layer to the substrate to the height of the formed microneedles; (b) patterning a metal layer onto the surface of the sacrificial polymer layer of polymeric material to form a patterned etch mask; and (c) using reactive ion etching to shape the tip portion of the microneedles. The patterned etch mask can be placed asymmetrically over the microneedles, effective to form microneedles having a beveled tip, or placed symmetrically over the microneedles, effective to form microneedles having a symmetrical tapered tip.

BRIEF DESCRIPTION OF THE FIGURES

FIG. 3 is a cross-sectional view of one embodiment of a device having microneedles formed of multiple layers of different polymeric materials.

FIGS. 6*a-g* illustrate a process of fabricating hollow polymeric microneedles, shown in cross-section, using a combination of photolithography and micromolding.

FIGS. 8*a-i* illustrate a process of fabricating solid polymeric microneedles having a beveled tip, shown in cross-section, using a combination of photolithography and micromolding.

DETAILED DESCRIPTION OF THE INVENTION

1. Biological Barriers

Figure 1A:
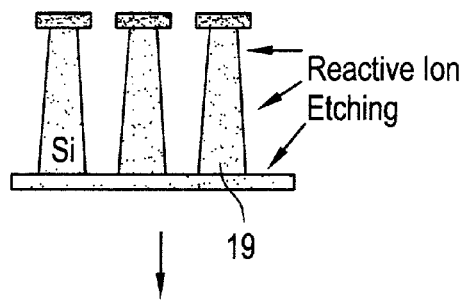
FIGS. 1*a-g* illustrate a process of fabricating polymer microneedles, shown in cross-section, using a silicone mold.
Figure 1G:
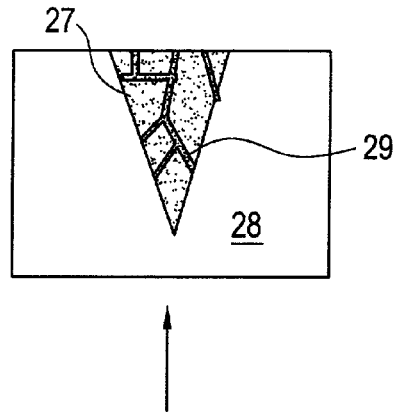
Figure 1B:
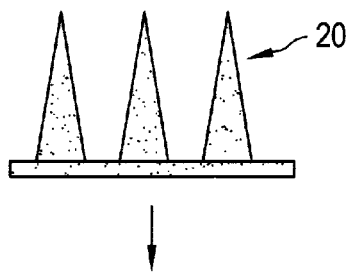
Figure 1F:
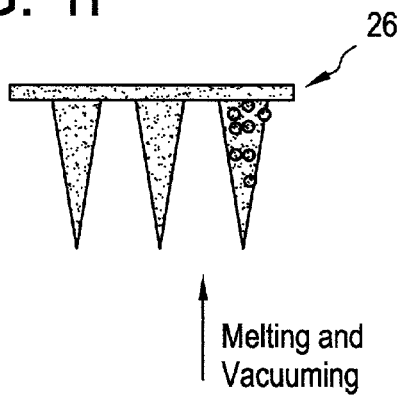
Figure 1C:
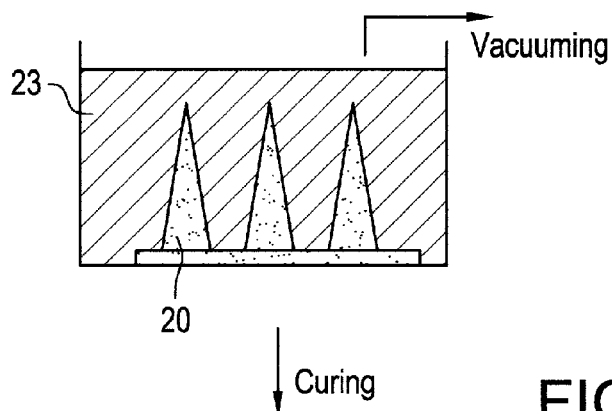
Figures 1D, 1E:
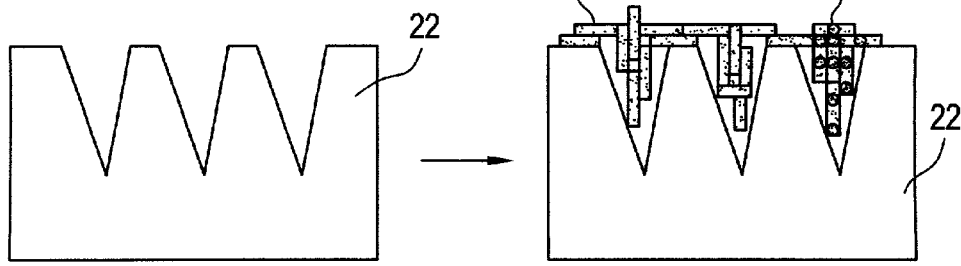
Figure 2A:
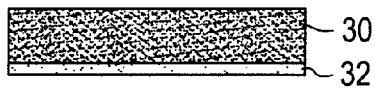
FIGS. 2*a-g* illustrate a process of fabricating polymer microneedles, shown in cross-section, using reactive ion etching.
Figure 2B:
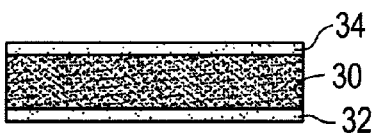
Figure 2C:
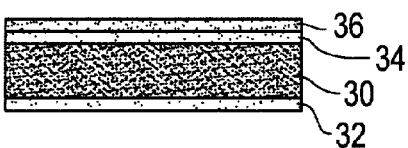
Figure 2D:
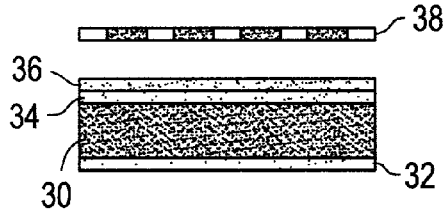
Figure 2E:
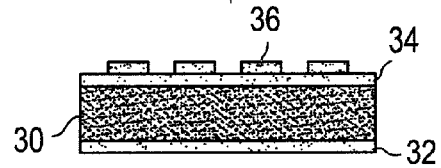
Figure 2F:
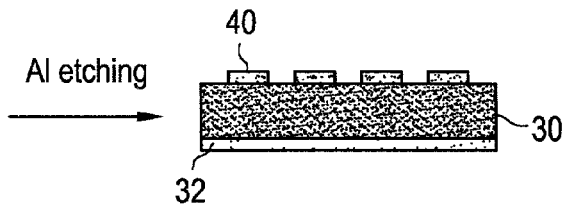
Figure 2G:
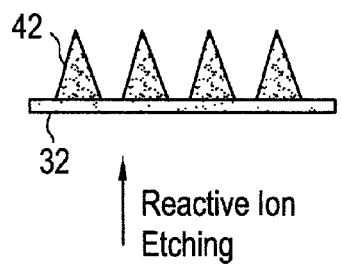

The devices disclosed herein are useful in transport of material into or across biological barriers including the skin (or parts thereof); the blood-brain barrier; mucosal tissue (e.g., oral, nasal, ocular, vaginal, urethral, gastrointestinal, respiratory); blood vessels; lymphatic vessels; or cell membranes (e.g., for the introduction of material into the interior of a cell or cells). The biological barriers can be in humans or other types of animals, as well as in plants, insects, or other organisms, including bacteria, yeast, fungi, and embryos. The microneedle devices can be applied to tissue internally with the aid of a catheter or laparoscope. For certain applications, such as for drug delivery to an internal tissue, the devices can be surgically implanted.

In a preferred embodiment, the microneedle device disclosed herein is applied to skin. The stratum corneum is the outer layer, generally between 10 and 50 cells, or between 10 and 20 µm thick. Unlike other tissue in the body, the stratum corneum contains "cells" (called keratinocytes) filled with bundles of cross-linked keratin and keratohyalin surrounded by an extracellular matrix of lipids. It is this structure that is believed to give skin its barrier properties, which prevents therapeutic transdermal administration of many drugs. Below the stratum corneum is the viable epidermis, which is between 50 and 100 µm thick. The viable epidermis contains no blood vessels, and it exchanges metabolites by diffusion to and from the dermis. Beneath the viable epidermis is the dermis, which is between 1 and 3 mm thick and contains blood vessels, lymphatics, and nerves.

As used herein, references to using the microneedle devices on "skin" also include using the microneedle devices with other biological barriers unless expressly limited to only skin.

2. The Microneedle Device

The microneedle devices disclosed herein include a substrate; one or more microneedles; and, optionally, a reservoir for delivery of drugs or collection of analyte. The devices also can include one or more pumps (or other mechanisms for inducing flow through needle bores, channels or pores), sensors, and/or microprocessors to control the interaction of the foregoing.

a. Substrate

The substrate of the device can be constructed from a variety of materials, including metals, ceramics, semiconductors, organics, polymers, and composites. Polymers, copolymers, blends, and composites of polymers with other materials are preferred. The substrate includes the base to which the microneedles are attached or integrally formed. One or more reservoirs may also be attached to, or formed in, the substrate.

In one embodiment of the device, the substrate is formed from a thin, rigid material that is sufficiently stiff to force the microneedles through the biological barrier in such areas where the barrier resists deformation by the microneedles. In another embodiment of the device, the substrate is formed from flexible materials to allow the device to fit the contours of the biological barrier, and to adapt to barrier deformations that may occur when the microneedle device is applied. A flexible device may facilitate more consistent penetration during use, since penetration can be limited by deviations in the attachment surface. For example, the surface of human skin is not flat due to dermatoglyphics, i.e. tiny wrinkles, and hair, and is highly deformable. The flexible substrate can be deformed mechanically (for example, using an actuator or simply by fluid pressure) in order to pierce the biological barrier.

b. Microneedle

The microneedles can be oriented perpendicular or at an angle to the substrate. Preferably, the microneedles are oriented perpendicular to the substrate so that a larger density of microneedles per unit area of substrate is provided. An array of microneedles can include a mixture of microneedle orientations, heights, or other parameters.

Materials of Construction

The microneedles of the device can be constructed from a variety of materials, including metals, ceramics, semiconductor materials, and composites, but preferably are formed of a polymer, particularly a biocompatible polymer. The polymer can be biodegradable or non-biodegradable. Examples of suitable biocompatible, biodegradable polymers include poly (lactide)s, poly(glycolide)s, poly(lactide-co-glycolide)s, polyanhydrides, polyorthoesters, polyetheresters, polycaprolactones, polyesteramides, poly(butyric acid), poly(valeric acid), polyurethanes and copolymers and blends thereof. Biodegradable hydrogels also be useful as a matrix material. Representative non-biodegradable polymers include polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

In one embodiment, the microneedle includes or is formed of drug. For example, drug particles can be dispersed in a polymer liquid or polymer solution which is then micromolded. In another example, the drug molecules are encapsulated or linked with the material forming the microneedle structure, for example, a biodegradable polymer. In one specific embodiment of this example, the drug is a vaccine and the matrix material (forming the needle structure) degrades into adjuvants useful for the vaccine. In yet another example, the microneedle is composed of a drug material. Other additives or excipient materials can be included in the microneedle structure and are described below.

In a preferred embodiment, the microneedle is formed from two or more materials. The two (or more) materials can be combined heterogeneously or as a homogeneous mixture. For example, the materials can be different metals, different polymers, or combinations of metals and polymers. For example, in the heterogeneous embodiments, the materials can be built up in layers, such that the composition varies along the shaft of the microneedle, or the microneedle can have a core of a first material with a coating of a second material formed onto the core. Additional layers of the first or other materials could also be included onto the second material. In another variation, the second material is filled into voids or pores within a matrix of the first material.

Structure

Generally, the microneedles should have the mechanical strength to remain intact for delivery of drugs or for serving as a conduit for the collection of biological fluid, while being inserted into the skin, while remaining in place for seconds up to a number of days, and while being removed. In embodiments where the microneedles are formed of biodegradable polymers and/or drugs, however, the microneedles or tips thereof can be intentionally broken off, for example in the skin, and will biodegrade and release drug. Biodegradable hollow or porous microneedles that provide a conduit function should remain intact long enough to deliver or withdraw the desired quantity of molecules. Biodegradable microneedles can provide an increased level of safety compared to nonbiodegradable ones, such that they are essentially harmless even if inadvertently broken off into the skin. This applies whether the microneedles contain molecules for delivery or serve merely a conduit function.

The microneedles can be formed of a nonporous or porous solid (with or without a sealed coating or exterior portion), and can be hollow. As used herein, the term "porous" means having pores or voids throughout at least a portion of the microneedle structure, sufficiently large and sufficiently interconnected to permit passage of fluid and/or solid materials into or through the microneedle. As used herein, the term "hollow" means having one or more bores or channels through the interior and along a substantial portion of the length of the microneedle structure, having a diameter sufficiently large to permit passage of fluid and/or solid materials through the microneedle. The bores are preferably annular, and may extend throughout all or a portion of the needle in the direction of the tip to the base, extending parallel to the direction of the needle or branching or exiting at a side of the needle, as appropriate. A solid or porous microneedle can be hollow. One of skill in the art can select the appropriate porosity and/or bore features required for specific applications. For example, one can adjust the pore size or bore diameter to permit passage of the particular material to be transported through the microneedle device. The inner surface of the bore of hollow microneedles can be made rough to enhance cell membrane disruption for those applications in which cell disruption is useful.

In a preferred embodiment, the exterior surface of the microneedle shaft includes one or more channels (i.e. a notch or groove) extending longitudinally along the shaft. The channel can serve as a conduit, for drug delivery or fluid withdrawal, following insertion of the microneedle into a biological barrier. Alternatively, the channel can be filled with a matrix material containing a drug or with a biosensor. The drug would then be released at a controlled rate following microneedle insertion, by diffusion of the drug from the matrix, degradation of the matrix material, or a combination thereof.

In another embodiment, the microneedle includes a closed bore. By closed bore is meant that the microneedle includes an opening at the needle tip which extends into the shaft of the microneedle and terminates at or near the base of the microneedle. This closed bore can be loaded with a drug or a matrix material that includes drug, such that the drug can be released from the bore opening following microneedle insertion. The drug would then be released at a controlled rate by diffusion of the drug from the matrix, degradation of the matrix material, or a combination thereof. The closed bore alternatively could include a biosensor or be used in sensing or fluid withdrawal.

Alternatively, the bore could be closed at the tip, so that bore is exposed (opened) only upon intentionally breaking off the microneedles following insertion. This might be useful for delivery of the molecules inside the bore to skin surface.

In the channel and closed bore embodiments, the drug matrix material (in the bore or channel) preferably can be selected without considering its mechanical strength properties, as the remainder of the microneedle structure can provide the mechanical strength needed to penetrate the biological barrier. In addition, in the channel and closed bore embodiments, the rate of drug delivery can be controlled by selecting different size bores or channels and/or different matrix materials.

In another embodiment, polymer microneedles are reinforced with metal to provide additional structural strength. This could be achieved by fabricating a metal core with a polymer coating around it. This could also be achieved with a lattice of metal within a polymer needle. In this way, the polymer material can be selected based on drug delivery, biocompatibility and other considerations, while the metal is selected based on mechanical considerations.

The microneedles can have straight or tapered shafts. In one embodiment, the diameter of the microneedle is greatest at the base end of the microneedle and tapers to a point at the end distal the base. The microneedle can also be fabricated to have a shaft that includes both a straight (untapered) portion and a tapered portion. The microneedles can be formed with shafts that have a circular cross-section in the perpendicular, or the cross-section can be non-circular. For example, the cross-section of the microneedle can be polygonal (e.g. star-shaped, square, triangular), oblong, or another shape.

The tip portion of the microneedles can have a variety of configurations. The tips can be symmetrical or asymmetrical about the longitudinal axis of the microneedle shaft. In a preferred embodiment, the tips are beveled. In another embodiment, the tip portion is tapered. In one embodiment, the tapered tip portion is in the shape of a pyramid on a shaft portion having a square cross-section, such that the microneedle is in the shape of an obelisk. Of course, the tip and/or shaft can be rounded, or have another shape, as well. The tip portion preferably has a height that is less than 50% of the height of the height of the microneedle. The beveled or obelisk structures advantageously provides better mechanical properties than fully tapered microneedles.

Dimensions

The microneedles preferably have a width or cross-sectional dimension between about 1 µm and 500 µm, more preferably between 10 µm and 100 µm. For hollow microneedles, the outer diameter or width is typically between about 10 µm and about 100 µm, and the inner diameter is typically between about 3 µm and about 80 µm.

The length of the microneedle can be selected for the particular application, and typically would account for both an inserted and uninserted portion. Shorter microneedles would be useful for example for penetrating individual cells or penetrating just into the stratum corneum. In contrast, the longer needles might be useful for example for penetrating into the dermis. The methods described herein enable one to make a particular size needed for a particular application.

In some embodiments, the microneedles have length of at least about 30 microns (e.g., at least about 50 microns, at least about 100 microns, at least about 250 microns). In certain embodiments, the microneedles have a length of at most about 1000 microns (e.g., at most about 900 microns, at most about 800 microns, at most about 700 microns, at most about 600 microns, at most about 500 microns.

In other embodiments, the microneedles have length of at least about 500 microns (e.g., at least about 600 microns, at least about 700 microns, at least about 800 microns, at least about 900 microns). In certain embodiments, the microneedles have a length of at most about 1500 microns (e.g., at most about 1400 microns, at most about 1300 microns, at most about 1200 microns, at most about 1000 microns). Exemplary ranges for microneedle lengths include, from about 800 microns to about 1100 microns (e.g., from about 900 microns to about 1000 microns, from about 930 microns to about 970 microns, about 950 microns).

The microneedles preferably are fabricated to have an aspect ratio 1:10 and 1:100, more preferably between about 1:2 and 1:20, and more preferably between about 1:3 and 1:10.

An array of microneedles can include a mixture of microneedles having, for example, various lengths, outer diameters, inner diameters, cross-sectional shapes, and spacing between the microneedles.

c. Reservoir

The microneedle device may include a reservoir in communication with the microneedles. The reservoir can be attached to the substrate by any suitable means. In a preferred embodiment, the reservoir is attached to the back of the substrate (opposite the microneedles) around the periphery, using an adhesive agent (e.g., glue). A gasket may also be used to facilitate formation of a fluid-tight seal.

In a preferred embodiment, the reservoir contains drug for delivery through the microneedles. The reservoir may be a hollow vessel, a porous matrix, or a solid form including drug which is transported therefrom. The reservoir can be formed from a variety of materials that are compatible with the drug or biological fluid contained therein. Preferred materials include natural and synthetic polymers, metals, ceramics, semiconductors, organics, and composites. In one embodiment, the reservoir is a standard syringe.

The microneedle device can include one or a plurality of chambers for storing materials to be delivered. In the embodiment having multiple chambers, each can be in fluid connection with all or a portion of the microneedles of the device array. In one embodiment, at least two chambers are used to separately contain drug (e.g., a lyophilized drug, such as a vaccine) and an administration vehicle (e.g., saline) in order to prevent or minimize degradation during storage. Immediately before use, the contents of the chambers are mixed. Mixing can be triggered by any means, including, for example, mechanical disruption (i.e. puncturing or breaking), changing the porosity, or electrochemical degradation of the walls or membranes separating the chambers. In another embodiment, a single device is used to deliver different drugs, which are stored separately in different chambers. In this embodiment, the rate of delivery of each drug can be independently controlled.

In a preferred embodiment, the reservoir should be in direct contact with the microneedles and have holes through which drug could exit the reservoir and flow into the interior of hollow or porous microneedles. In another embodiment, the reservoir has holes which permit the drug to transport out of the reservoir and onto the skin surface. From there, drug is transported into the skin, either through hollow or porous microneedles, along the sides of microneedles, or through pathways created by microneedles in the skin.

d. Transport Control Components

The microneedle device also must be capable of transporting material across the barrier at a useful rate. For example, the microneedle device must be capable of delivering drug across the skin at a rate sufficient to be therapeutically useful. The device may include a housing with microelectronics and other micromachined structures to control the rate of delivery either according to a preprogrammed schedule or through active interface with the patient, a healthcare professional, or a biosensor. The rate can be controlled by manipulating a variety of factors, including the characteristics of the drug formulation to be delivered (e.g., its viscosity, electric charge, and chemical composition); the dimensions of each microneedle (e.g., its outer diameter and the area of porous or hollow openings); the number of microneedles in the device; the application of a driving force (e.g., a concentration gradient, a voltage gradient, a pressure gradient); and the use of a valve. Alternatively, the rate of delivery can be controlled by selecting the rate of biodegradation or dissolution of the microneedles formed of drug or formed of a biodegradable matrix having drug dispersed within the matrix, for example by selection of the appropriate polymeric matrix material.

The rate also can be controlled by interposing between the drug in the reservoir and the opening(s) at the base end of the microneedle polymeric or other materials selected for their diffusion characteristics. For example, the material composition and layer thickness can be manipulated using methods known in the art to vary the rate of diffusion of the drug of interest through the material, thereby controlling the rate at which the drug flows from the reservoir through the microneedle and into the tissue.

Transportation of molecules through the microneedles can be controlled or monitored using, for example, various combinations of valves, pumps, sensors, actuators, and microprocessors. These components can be produced using standard manufacturing or microfabrication techniques. Actuators that may be useful with the microneedle devices disclosed herein include micropumps, microvalves, and positioners. In one embodiment, a microprocessor is programmed to control a pump or valve, thereby controlling the rate of delivery.

Flow of molecules through the microneedles can occur based on diffusion, capillary action, or can be induced using conventional mechanical pumps or nonmechanical driving forces, such as electroosmosis or electrophoresis, or convection. For example, in electroosmosis, electrodes are positioned on the biological barrier surface, one or more microneedles, and/or the substrate adjacent the needles, to create a convective flow which carries oppositely charged ionic species and/or neutral molecules toward or into the biological barrier. In a preferred embodiment, the microneedle device is used in combination with another mechanism that enhances the permeability of the biological barrier, for example by increasing cell uptake or membrane disruption, using electric fields, ultrasound, chemical enhancers, vacuum viruses, pH, heat and/or light.

Passage of the microneedles, or drug to be transported via the microneedles, can be manipulated by shaping the microneedle surface, or by selection of the material forming the microneedle surface (which could be a coating rather than the microneedle per se). For example, one or more grooves on the outside surface of the microneedles can be used to direct the passage of drug, particularly in a liquid state. Alternatively, the physical surface properties of the microneedle can be manipulated to either promote or inhibit transport of material along the microneedle surface, such as by controlling hydrophilicity or hydrophobicity.

The flow of molecules can be regulated using a wide range of valves or gates. These valves can be the type that are selectively and repeatedly opened and closed, or they can be single-use types. For example, in a disposable, single-use drug delivery device, a fracturable barrier or one-way gate may be installed in the device between the reservoir and the opening of the microneedles. When ready to use, the barrier can be broken or gate opened to permit flow through the microneedles. Other valves or gates used in the microneedle devices can be activated thermally, electrochemically, mechanically, or magnetically to selectively initiate, modulate, or stop the flow of molecules through the needles. In a preferred embodiment, flow is controlled by using a rate-limiting membrane as a "valve."

The microneedle devices can further include a flowmeter or other means to monitor flow through the microneedles and to coordinate use of the pumps and valves.

e. Sensors

Useful sensors may include sensors of pressure, temperature, chemicals, and/or electro-magnetic fields. Biosensors can be located on the microneedle exterior surface (e.g., in a channel), inside a microneedle (inside a bore or pores), or inside a device in communication with the body tissue via the microneedle (solid, hollow, or porous). These microneedle biosensors can include four classes of principal transducers: potentiometric, amperometric, optical, and physiochemical. An amperometric sensor monitors currents generated when electrons are exchanged between a biological system and an electrode. Blood glucose sensors frequently are of this type.

The microneedle may function as a conduit for fluids, solutes, electric charge, light, or other materials. In one embodiment, hollow microneedles (or those having a bore or channel) can be filled with a substance, such as a gel, that has a sensing functionality associated with it. In an application for sensing based on binding to a substrate or reaction mediated by an enzyme, the substrate or enzyme can be immobilized in the needle interior, which would be especially useful in a porous needle to create an integral needle/sensor.

Wave guides (e.g., PMMA) can be incorporated into the microneedle device to direct light to a specific location, or for detection, for example, using means such as a pH dye for color evaluation. Similarly, heat, electricity, light or other energy forms may be precisely transmitted to directly stimulate, damage, or heal a specific tissue or intermediary (e.g., tattoo removal for dark skinned persons), or diagnostic purposes, such as measurement of blood glucose based on IR spectra or by chromatographic means, measuring a color change in the presence of immobilized glucose oxidase in combination with an appropriate substrate.

f. Attachment Features

A collar or flange also can be provided with the device, for example, around the periphery of the substrate or the base. It preferably is attached to the device, but alternatively can be formed as an integral part of the substrate, for example by forming microneedles only near the center of an "oversized" substrate. The collar can also emanate from other parts of the device. The collar can provide an interface to attach the microneedle array to the rest of the device, and can facilitate handling of the smaller devices.

In a preferred embodiment, the microneedle device includes an adhesive to temporarily secure the device to the surface of the biological barrier. The adhesive can be essentially anywhere on the device to facilitate contact with the biological barrier. For example, the adhesive can be on the surface of the collar (same side as microneedles), on the surface of the substrate between the microneedles (near the base of the microneedles), or a combination thereof.

In one embodiment, the microneedle device is incorporated into an arm (e.g., wrist) band. The armband can be conveniently worn by a patient for drug delivery, sampling of biological fluids, or both over a prolonged period, such as several hours.

g. Additives/Excipient Materials Used in Forming the Microneedles

The microneedles can include an additive which (1) is removed before insertion of the microneedles into the biological barrier; (2) is removed while the microneedles are inserted in the biological barrier; or (3) remains in the microneedle.

The first function above is used in the making of porous microneedles. Voids are formed in the microneedles upon removal of the pore forming agent additive before insertion. The selection of pore forming agent is based on its physical or chemical properties required for removal (e.g., solubility, volatilization or melting temperature) and compatibility with the polymer and/or drug, for example. Preferably, the pore forming agent is immiscible in the main structural component of the microneedle (e.g., polymer), and is biocompatible or at least leaves only biocompatible residues, if any. Representative pore forming agents include sodium chloride, sodium phosphate, sodium carbonate, potassium chloride, and volatile salts, such as ammonium bicarbonate, ammonium acetate, ammonium chloride, ammonium benzoate and mixtures thereof, as well as iodine, phenol, benzoic acid (as acid not as salt), and naphthalene. Other examples of specific salts include $Na_2HPO_4$, $Na_2HPO_4$-$12H_2O$ (a salt hydrate), and $K_2HPO_4$. Salts listed as pharmaceutical excipients approved by the FDA are typically preferred. Several classes of compounds other than salt also can be used.

The use of a hydrate may be preferred. In hydrates, the water dissociates from the salt at a given temperature. Thus, below that dissociation temperature, the hydrate is a solid. Above that temperature, the water dissociates and forms liquid water, which can dissolve some or all of the salt. Thus, you can get a solid to liquid phase transition. In the case of $Na_2HPO_4$-$12H_2O$, this transition occurs just below body temperature. Thus, the hydrate is solid at room temperature (assuming it is not too hot), but becomes liquid at body temperature. This is useful for forming voids. These voids could be formed during processing by raising the temperature. They could be formed in the body. If so, the formulation should probably be stored in the refrigerator to prevent a premature phase change. These voids could be useful as transport pathways (porous/hollow needle) or plugs removed to initiate drug release. The hydrates could also be structurally reinforcing agents which disappear after insertion into the body, thus preventing re-use.

The second function is one where the additive is left in the microneedle and removed after insertion. For example, the additive can be a salt that is dissolved away upon contact with water in the biological barrier. The removal of the additive can initiate release of drug that is stored within the microneedles or in a reservoir in communication with the microneedles. The release kinetics can be controlled, for example, by selection of the rate of dissolution and/or degradation of the additive and/or polymer. For example, the bulk of the microneedle can be a slowly- or non-degradable polymer having dispersed therein rapidly-degradable polymer particles. The additive may function to enhance the structural strength of the microneedles, but only for a single insertion (e.g. to enhance safety by rendering the microneedles unsuitable for reuse/misuse). Then, following insertion, the additive dissolves away to render the microneedles too weak to penetrate the biological barrier without structural failure. The additive for this function should be soluble or degradable upon contact with the biological fluids present in the biological barrier to be penetrated. The additive is selected, for example, based on the pH and temperature of these aqueous fluids.

In the third function, the additive remains, typically to serve a structural function (i.e. to lend mechanical strength or rigidity to the microneedles). For example, a dispersion of rigid salt particles in PLGA can enhance the rigidity of PLGA microneedles. Representative examples of suitable such materials include water insoluble inorganic materials, such as aluminum hydroxide, aluminum phosphate, and zinc oxide.

Generally, additive particles should be sufficiently small that they do not alter the exterior shape of the microneedles. Particles of additives typically are much smaller than the dimensions of the microneedles, for example, so they can form numerous microdomains within a continuous polymeric matrix. In another embodiment, there are sequential domains of polymer and additive (e.g., layers of polymer separated by layers of additive), in a laminate structure. In a further embodiment, the bores of hollow microneedles are filled with additive, forming a temporary plug which dissolves upon insertion, thereby permitting release of drug through the bore. The additive, e.g., salt, in this embodiment provides two functions: it enhances the structural rigidity of the microneedles during insertion and prevents leakage of drug before use.

The additive is selected based on its ability to be removed and/or its ability to alter the structural properties of the microneedle. Removal can be conducted in several ways, for example, by a phase change, such as dissolution, degradation, vaporization, liquefaction, or a combination thereof. In one embodiment, the needles are made under conditions where the main material and the needle are both solids. Upon warming, the additive changes phase (e.g., melt) but the bulk material forming the microneedle structure does not. For example, the additive can be ice which is subsequently melted. Another option is that a hydrate is used. Below a certain temperature, the hydrate is intact and above that temperature, the water dissociates from the other material (e.g., salt). Alternatively, the additive is a gel sensitive to temperature, pH, or another stimuli. Many triggers are possible for inducing a phase change which can cause the additive to be removed, either during processing or within the body. One of skill in the art can select the appropriate material/structure for the particular application. See, for example, Pettifor, *Bonding and Structure of Molecules and Solids*, (New York, Oxford University Press 1995); Hull & Clyne, *An Introduction to Composite Materials* (2d ed., New York, Cambridge University Press 1996).

h. Molecules to Be Delivered

Essentially any drug can be delivered using the microneedle devices described herein. As used herein, the term "drug" refers to an agent which possesses therapeutic, prophylactic, or diagnostic properties in vivo, for example when administered to an animal, including mammals, such as humans. This includes ex vivo or in vitro delivery into cells or single cell animals. Examples of suitable therapeutic and/or prophylactic active agents include proteins, such as hormones, antigens, and growth factors; nucleic acids, such as antisense molecules; and smaller molecules, such as antibiotics, steroids, decongestants, neuroactive agents, anesthetics, and sedatives. Examples of suitable diagnostic agents include radioactive isotopes and radioopaque agents, metals, gases, labels including chromatographic, fluorescent or enzymatic labels.

A preferred drug is a vaccine. The term vaccine includes viral or DNA substituents, for therapeutic or prophylactic applications.

The drug can be or include a peptide, protein, carbohydrate (including monosaccharides, oligosaccharides, and polysaccharides), nucleoprotein, mucoprotein, lipoprotein, glycoprotein, nucleic acid molecules (including any form of DNA such as cDNA, RNA, or a fragment thereof, oligonucleotides, and genes), nucleotide, nucleoside, lipid, biologically active organic or inorganic molecules, or combination thereof.

The amount of drug can be selected by one of skill in the art, based, for example on the particular drug, the desired effect of the drug at the planned release levels, and the time span over which the drug should be released.

Other agents which can be released include perfumes, insect repellents, sun block, and dyes or other coloring agents.

Essentially any drug can be incorporated into microneedles formed of other materials, so long as the drug can survive the fabrication process conditions to which it is exposed following its introduction into the process, for example, high or low temperatures and pressures and exposure to solvents and mechanical forces. For example, drugs that can be impregnated in polymeric microneedles are those known to be capable of incorporation into polymeric microspheres.

The selection of drugs capable of formation into microneedles, however, is more limited. The drug preferably is a solid or capable of being made into a solid. It is envisioned, however, that the drug also can be a liquid or gel.

i. Transdermal Microneedle Device

Figure 5:
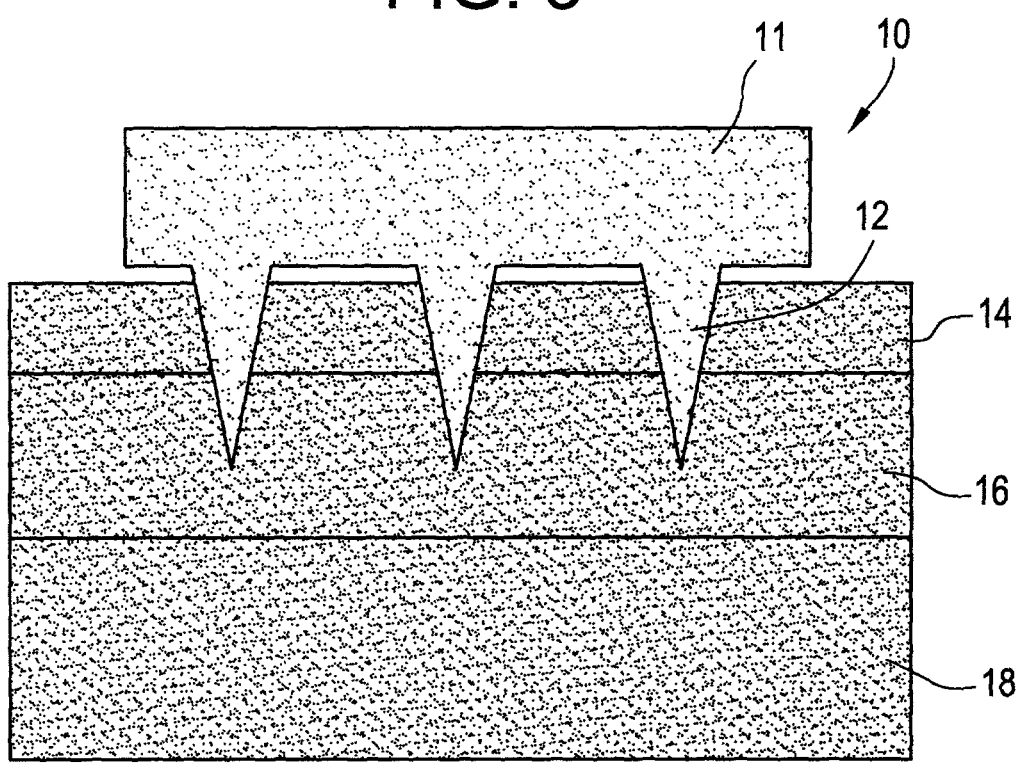
FIG. 5 is a side elevational view of a schematic of an embodiment of the microneedle device inserted into undeformed skin.

FIG. 5 is a side elevational view of a schematic of an embodiment of the microneedle device inserted into undeformed skin. The device 10 includes an upper portion or substrate 11 from which a plurality of microneedles 12 protrude. The upper portion 11 of the device can be solid or hollow, and may include multiple compartments. In a preferred embodiment for drug delivery, the upper portion 11 contains one or more drugs to be delivered. It is also preferred that the upper portion include one or more sensors and/or an apparatus (e.g., pump or electrode) to drive provide/direct the force) transport of the drug or other molecules.

The diameter and length of the microneedle both affect pain as well as functional properties of the needles. In one embodiment for transdermal applications, the "insertion depth" of the microneedles 12 is less than about 100 µm, more preferably about 30 µm, so that insertion of the microneedles 12 into the skin through the stratum corneum 14 does not penetrate through the epidermis 16 into the dermis 18 (as described below), thereby avoiding contacting nerves and reducing the potential for causing pain. In such applications, the actual length of the microneedles may be longer, since the portion of the microneedles distal the tip may not be inserted into the skin; the uninserted length depends on the particular device design and configuration. The actual (overall) height or length of microneedles 12 should be equal to the insertion depth plus the uninserted length. Other embodiments using sufficiently small microneedles may penetrate into the dermis without causing pain. In alternative embodiments, the microneedle length and/or penetration depth may be greater than illustrated, for example for the delivery of vaccine to dendritic cells at the dermis interface. The microneedles 12 can be solid or porous, and can include one or more bores connected to upper portion 11.

3. Methods of Making Microneedle Devices

The microneedle devices are made by microfabrication processes that are based on established methods used to make integrated circuits, electronic packages and other microelectronic devices, augmented by additional methods used in the field of micromachining and micromolding. Three-dimensional arrays of microneedles can be fabricated, for example, using combinations of dry etching processes; micromold creation in lithographically-defined polymers and selective sidewall electroplating; or direct micromolding techniques using epoxy mold transfers. These processes are described in U.S. Ser. No. 09/095,221, filed Jun. 10, 1998, and U.S. Ser. No. 09/316,229, filed May 21, 1999, by Prausnitz, et al., and in PCT WO 99/64580 and PCT WO 00/74763, and are incorporated herein by reference, with preferred and additional methods described below.

Polymer microneedles can be fabricated by (i) etching the polymer microneedle directly, (ii) etching a mold and then filling the mold to form the polymer microneedle product, or (iii) etching a microneedle master, using the master to make a mold, and then filling the mold to form the polymer microneedle replica (of the master). Details of these processes are described below.

Micromolding

One method for forming microneedles is to use microfabrication techniques such as photolithography, plasma etching, or laser ablation to make a mold form (A), transferring that mold form to other materials using standard mold transfer techniques, such as embossing or injection molding (B), and reproducing the shape of the original mold form (A) using the newly-created mold (B) to yield the final microneedles (C). Alternatively, the creation of the mold form (A) could be skipped and the mold (B) could be microfabricated directly, which could then be used to create the final microneedles (C).

In a preferred method, polymeric microneedles are made using microfabricated molds. For example, epoxy molds can be made as described above and injection molding techniques can be applied to form the microneedles in the molds (Weber, et al., "Micromolding—a powerful tool for the large scale production of precise microstructures", Proc. SPIE-*International Soc. Optical Engineer.* 2879:156-67 (1996); Schift, et al., "Fabrication of replicated high precision insert elements for micro-optical bench arrangements" Proc. SPIE-*International Soc. Optical Engineer.* 3513:122-34 (1998)). These micromolding techniques may be preferred over other techniques, as they may provide relatively less expensive replication, i.e. lower cost of mass production. In a preferred embodiment, the polymer is biodegradable.

In one embodiment, micromolds are filled with liquid monomer or a solution of monomer, the monomer is polymerized, and the polymer is directly or indirectly converted to a solid form in the shape of the microneedles. Alternatively, the micromold is filled with polymer powder, heated to melt the polymer, and then cooled to solidify the polymer in the shape of the microneedles. The polymer powder also can be molded by compression molding. In a preferred embodiment, polymer melting is conducted under reduced pressure (e.g., vacuum conditions) in order to pull the polymer into the mold and displace any trapped gases, thereby minimizing or eliminating the formation of void defects in the microneedles. Polymer can also be pulled into the mold by centrifugation. This approach overcomes the surface tension/wetting problems which can occur in large scale molding operations.

FIG. 1 illustrates the steps used in one method of molding polylactide or polylactide/glycolide microneedles using a silicone mold. The silicone mold is made by first forming a mold insert, i.e. an array of microneedles made by any method, e.g., reactive ion etching (RIE) a substrate having chromium masking (FIG. 1a). The mold insert (FIG. 1b) is then covered with polydimethylsiloxane (PDMS), under vacuum conditions to remove bubbles which can form and be trapped between the PDMS and insert (FIG. 1c). The PDMS is then cured to form a silicone mold. The microneedles are removed from the mold, rendering the mold ready to use to mold other microneedles (FIG. 1d). The silicone mold is then filled with glycolide or polylactide/glycolide powder (with or without sodium chloride powder mixed therein) (FIG. 1e). The polymer powder is then melted and/or compressed, preferably under vacuum, thereby forming polymer microneedles. Then, the polymer is cooled, and the microneedles are removed from the mold (FIG. 1f). The NaCl can function as a reinforcing structure, yielding added mechanical strength, or as a pore-forming agent which is dissolved out to leave a polymer having an open pore structure (FIG. 1g) as further described herein.

In certain embodiments, a micromold is filled in a two-step process, wherein the first step includes coating a first layer of a first material into the mold and solidifying the first material, and the second step includes filling the remainder of the mold with a second material. The process results in microneedles having an outer surface coating of the first material covering a core of the second material. This is particularly useful to avoid a burst release effect in drug delivery. For example, the first material could be a polymer coating and the second material could be a drug/polymer mixture, whereby the outer coating controls the time and/or rate of release of drug from the microneedle.

Microfabrication

Microneedles can be fabricated by (i) etching the microneedles directly, (ii) etching a mold and then filling the mold to form the microneedle product, or (iii) etching a microneedle master, using the master to make a mold, and then filling the mold to form the microneedle replica (of the master). The Examples below illustrate various embodiments of these techniques.

Microcutting/Microshaping

Rather than using chemical etching processes (e.g., RIE, photolithography) to define the microneedle or mold shape, special physical cutting tools with very sharp tips/cutting edges can be used. This micronshaping approach can be used to directly make microneedles, or can be used to make molds which are used to make microneedles. To directly make microneedles, a substrate (e.g., a piece of polymer or metal) is cut using a small cutting tool, which could be, for example, a microdiamond profiled in a wedge shape. One or more of these tools are used to cut the substrate into the desired shape. To make microneedles from a mold, the mold is prepared in the same fashion as described above. Then, it is used by techniques described herein to be replicated in polymer.

Other variations of the fabrication process are described in the Examples below.

5. Microneedle Device Applications

The device may be used for single or multiple uses for rapid transport across a biological barrier or may be left in place for longer times (e.g., hours or days) for long-term transport of molecules. Depending on the dimensions of the device, the application site, and the route in which the device is introduced into (or onto) the biological barrier, the device may be used to introduce or remove molecules at specific locations.

As discussed above, FIG. 5 shows a side elevational view of a schematic of a preferred embodiment of the microneedle device 10 in a transdermal application. The device 10 is applied to the skin such that the microneedles 12 penetrate through the stratum corneum and enter the viable epidermis so that the tip of the microneedle at least penetrates into the viable epidermis. In a preferred embodiment, drug molecules in a reservoir within the upper portion 11 flow through or around the microneedles and into the viable epidermis, where the drug molecules then diffuse into the dermis for local treatment or for transport through the body. The needles also could be made and used to penetrate directly to or into the dermis.

To control the transport of material out of or into the device through the microneedles, a variety of forces or mechanisms can be employed. These include pressure gradients, concentration gradients, electricity, ultrasound, receptor binding, heat, chemicals, and chemical reactions. Mechanical or other gates in conjunction with the forces and mechanisms described above can be used to selectively control transport of the material.

In particular embodiments, the device should be "user-friendly." For example, in some transdermal applications, affixing the device to the skin should be relatively simple, and not require special skills. This embodiment of a microneedle may include an array of microneedles attached to a housing containing drug in an internal reservoir, wherein the housing has a bioadhesive coating around the microneedles. The patient can remove a peel-away backing to expose an adhesive coating, and then press the device onto a clean part of the skin, leaving it to administer drug over the course of, for example, several days.

a. Delivery of Drug and Other Molecules

Essentially any drug can be delivered using these devices. Drugs can be proteins, enzymes, polysaccharides, polynucleotide molecules, and synthetic organic and inorganic compounds. Representative agents include vaccines, anti-infectives, hormones, such as insulin, growth regulators, drugs regulating cardiac action or blood flow, and drugs for pain control. The drug can be for local treatment or for regional or systemic therapy. The following are representative examples, and disorders they are used to treat:

Calcitonin, osteoporosis; Enoxaprin, anticoagulant; Etanercept, rheumatoid arthritis; Erythropoietin, anemia; Fentanyl, postoperative and chronic pain; Filgrastin, low white blood cells from chemotherapy; Heparin, anticoagulant; Insulin, human, diabetes; Interferon Beta 1a, multiple sclerosis; Lidocaine, local anesthesia; Somatropin, growth hormone; and Sumatriptan, migraine headaches.

In this way, many drugs can be delivered at a variety of therapeutic rates. The rate can be controlled by varying a number of design factors, including, but not limited to, the outer diameter of the microneedle, the number and size of pores or channels in each microneedle, the number and size (i.e. length) of microneedles in an array, the structure, materials of construction and, permeability of the microneedle, the magnitude and frequency of application of the force driving the drug through the microneedle and/or the holes created by the microneedles. For example, devices designed to deliver drug at different rates might have more microneedles for delivery that is more rapid and fewer microneedles for less rapid delivery. As another example, a device designed to deliver drug at a variable rate could vary the driving force (e.g., pressure gradient controlled by a pump) for transport according to a schedule which was pre-programmed or controlled by, for example, the user or his doctor. The devices can be affixed to the skin or other tissue to deliver drugs continuously or intermittently, for durations ranging from a few seconds to several hours or days.

One of skill in the art can measure the rate of drug delivery for particular microneedle devices using in vitro and in vivo methods known in the art. For example, to measure the rate of transdermal drug delivery, human cadaver skin mounted on standard diffusion chambers can be used to predict actual rates. See Hadgraft & Guy, eds., *Transdermal Drug Delivery: Developmental Issues and Research Initiatives* (Marcel Dekker, New York 1989); Bronaugh & Maibach, *Percutaneous Absorption, Mechanisms—Methodology—Drug Delivery* (Marcel Dekker, New York 1989). After filling the compartment on the dermis side of the diffusion chamber with saline, a microneedle array is inserted into the stratum corneum; a drug solution is placed in the reservoir of the microneedle device; and samples of the saline solution are taken over time and assayed to determine the rates of drug transport.

In a preferred embodiment, biodegradable microneedles can be used as the entire drug delivery device. For example, the microneedles can be formed of a biodegradable polymer containing a dispersion of an active agent for local or systemic delivery. The agent could be released over time, according to a profile determined by the composition and geometry of the microneedles, the concentration of the drug and other factors. In this way, the drug reservoir is within the matrix of one or more of the microneedles.

In one variation of this embodiment, the microneedles may be purposefully sheared off from the substrate after penetrating the biological barrier. In this way, a portion of the microneedles would remain within or on the other side of the biological barrier and a portion of the microneedles and their substrate would be removed from the biological barrier. In the case of skin, this could involve inserting an array into the skin, manually or otherwise breaking off the microneedles, or the tip portion thereof, and then removing the substrate and base portion of the microneedles, if any. The portion of the microneedles which remains in the skin or other biological barrier then releases drug over time according to a profile determined by the composition and geometry of the microneedles, the concentration of the drug, and other factors. The release of drug from biodegradable microneedles can be controlled by the rate of polymer degradation. Complex release patterns can be provided using microneedles formed of multiple materials, for example by fabricating microneedles having multiple layers of drugs and/or matrices of different materials.

The microneedles can release drugs for local or systemic effect, or can release other agents, such as perfumes; insect repellent; sun block; and dyes or other coloring agents, useful for example in making tattoos.

Microneedle shape and content can be designed to control the breakage of microneedles. For example, an indentation can be introduced into microneedles either at the time of fabrication or as a subsequent step. In this way, microneedles preferentially break at the site of the indentation. Alternatively, a section of the microneedle can be fabricated of a material that dissolves (e.g., a salt) or is otherwise removed following insertion of the microneedle. This removal can be controlled to occur after a period following insertion, for example, by selecting a material that degrades or dissolves slowly in vivo. In one embodiment, the breakage of the microneedle from the substrate indicates that the treatment is complete, functioning as a timer in effect and indicating that the device backing should be removed and a new microneedle device applied elsewhere on the biological barrier.

Moreover, the size and shape of the portion of microneedles which break off can be controlled not only for specific drug release patterns, but also for specific interactions with cells in the body. For example, objects of a few microns in size are known to be taken up by macrophages. The portions of microneedles that break off can be controlled to be bigger or smaller than that to prevent uptake by macrophages or can be that size to promote uptake by macrophages, which can be desirable for delivery of vaccines.

b. Diagnostic Sensing of Body Fluids (Biosensors)

One embodiment of the devices described herein may be used to remove material from the body across a biological barrier, i.e. for minimally invasive diagnostic sensing. For example, fluids can be transported from interstitial fluid in a tissue into a reservoir in the upper portion of the device. The fluid can then be assayed while in the reservoir or the fluid can be removed from the reservoir to be assayed, for diagnostic or other purposes. For example, interstitial fluids can be removed from the epidermis across the stratum corneum to assay for glucose concentration, which should be useful in aiding diabetics in determining their required insulin dose. Other substances or properties that would be desirable to detect include lactate (important for athletes), oxygen, pH, alcohol, tobacco metabolites, and illegal drugs (important for both medical diagnosis and law enforcement).

The sensing device can be in or attached to one or more microneedles, or in a housing adapted to the substrate. Sensing information or signals can be transferred optically (e.g., refractive index) or electrically (e.g., measuring changes in electrical impedance, resistance, current, voltage, or combination thereof). For example, it may be useful to measure a change as a function of change in resistance of tissue to an electrical current or voltage, or a change in response to channel binding or other criteria (such as an optical change) wherein different resistances are calibrated to signal that more or less flow of drug is needed, or that delivery has been completed.

In one embodiment, one or more microneedle devices can be used for (1) withdrawal of interstitial fluid, (2) assay of the fluid, and/or (3) delivery of the appropriate amount of a therapeutic agent based on the results of the assay, either automatically or with human intervention. For example, a sensor delivery system may be combined to form, for example, a system which withdraws bodily fluid, measures its glucose content, and delivers an appropriate amount of insulin. The sensing or delivery step also can be performed using conventional techniques, which would be integrated into use of the microneedle device. For example, the microneedle device could be used to withdraw and assay glucose, and a conventional syringe and needle used to administer the insulin, or vice versa.

In an alternate embodiment, microneedles may be purposefully sheared off from the substrate after penetrating the biological barrier, as described above. The portion of the microneedles which remain within or on the other side of the biological barrier could contain one or more biosensors. For example, the sensor could change color as its output. For microneedles sheared off in the skin, this color change could be observed through the skin by visual inspection or with the aid of an optical apparatus.

The microneedles can also be used for aerosolization or delivery for example directly to a mucosal surface in the nasal or buccal regions or to the pulmonary system.

The microneedle devices disclosed herein also should be useful for controlling transport across tissues other than skin. For example, microneedles can be inserted into the eye across or into, for example, conjunctiva, sclera, and/or cornea, to facilitate delivery of drugs into the eye. Similarly, microneedles inserted into the eye can facilitate transport of fluid out of the eye, which may be of benefit for treatment of glaucoma. Microneedles may also be inserted into the buccal (oral), nasal, vaginal, or other accessible mucosa to facilitate transport into, out of, or across those tissues. For example, a drug may be delivered across the buccal mucosa for local treatment in the mouth or for systemic uptake and delivery. As another example, microneedle devices may be used internally within the body on, for example, the lining of the gastrointestinal tract to facilitate uptake of orally-ingested drugs or the lining of blood vessels to facilitate penetration of drugs into the vessel wall. For example, cardiovascular applications include using microneedle devices to facilitate vessel distension or immobilization, similarly to a stent, wherein the microneedles/substrate can function as a "staple-like" device to penetrate into different tissue segments and hold their relative positions for a period to permit tissue regeneration. This application could be particularly useful with biodegradable devices. These uses may involve invasive procedures to introduce the microneedle devices into the body or could involve swallowing, inhaling, injecting or otherwise introducing the devices in a non-invasive or minimally-invasive manner.

c. Delivery of Energy

Other than transport of drugs and biological molecules, the microneedles may be used to transmit or transfer other materials and energy forms, such as light, electricity, heat, or pressure. The microneedles, for example, could be used to direct light to specific locations within the body, in order that the light can directly act on a tissue or on an intermediary, such as light-sensitive molecules in photodynamic therapy.

The present invention will be further understood with reference to the following non-limiting examples.

EXAMPLE 1

Fabrication of Solid Polylactide Microneedles Using Molding

Solid silicon microneedle arrays were fabricated as previously described (S Henry, et al. (1998) "Microfabricated microneedles: A novel approach to transdermal drug delivery," *J. Pharm. Sci.* 87:922-25). The final steps of this process are shown in FIGS. 1*a* and 1*b*, with array of solid silicon microneedles 20 resulting from reactive ion etching of silicon substrate 19 with chromium masks 21.

Then, a polydimethylsiloxane (PDMS) mold of the silicon microneedle array was made under vacuum (FIG. 1*c*). After curing the PDMS 23 and removing the silicon microneedle array 20, a silicone mold 22 of the microneedles resulted (FIG. 1*d*). This mold was then filled either with polylactide or with polylactide (e.g., 90%) and NaCl (e.g., 10%) in solid form. FIG. 1*e* shows the left and center individual microneedle molds containing only polylactide particles 24 and the right individual microneedle mold containing a mixture of polylactide particles 24 and NaCl particles 25. Heating under vacuum melted the polylactide.

When salt was included, it was entrapped within the polylactide melt. After quenching, the polylactide needle array 26 was removed from the silicone mold (FIG. 1*f*). By placing in water, salt could be removed from the polylactide needles, leaving pores within the needles. FIG. 1*g* illustrates the right microneedle 27 in water 28, wherein a series of pores 29 have been formed.

Resulting polylactide microneedles were 200 microns long and 80 microns wide at their base, which was the same shape as the original silicon needles used to make the mold.

EXAMPLE 2

Fabrication of Solid PLA Microneedles Using RIE

A layer of polylactide 30 was coated onto a silicon or glass substrate 32 (FIG. 2*a*). A thin film of aluminum 34 was deposited on the upper surface of the polylactide layer 30 (FIG. 2*b*). Then, photoresist 36 was coated onto the upper surface of the aluminum film 34 (FIG. 2*c*). Ultraviolet (UV) light was then shined onto the photoresist through an optical mask 38 containing dark circles having the shape of the microneedle bases (FIG. 2*d*). The photoresist was then developed (FIG. 2*e*). The aluminum not covered by photoresist was then etched away and the remaining photoresist was removed (FIG. 2*f*). This left a pattern of aluminum dots 40 forming a physical mask having the same geometry as the optical mask. Finally, using reactive ion etching (RIE), the polylactide was etched; the aluminum mask defined the size of the microneedle base while the RIE gas composition defined the taper of the needles (FIG. 2*g*). Microneedles needles made in this fashion were solid and measured 80 microns at their base and 100 microns in length.

It should be noted that different layers of polymer could have been sequentially formed together as polymer layer 30, such that the resulting needles were formed of layers of different materials. For example, the tip portion could be formed of a first polymeric material having a lower rate of biodegradation than the base or shaft portion. FIG. 3 shows one example of microneedles formed by applying this etching technique to a multilayer polymer structure, yielding a device having microneedles formed of four different materials. The choice of materials can be selected to provide desired mechanical strength, degradation rates, release profiles, and other properties.

EXAMPLE 3

Fabrication of Hollow PLA Microneedles

SU-8 epoxy photoresist 60 was coated onto a silicon wafer substrate 62 containing an array of holes 64, which were 100 microns in diameter and etched into the silicon using deep reactive ion etching (FIG. 6*a*). UV was then exposed through a dark optical mask 66 containing transparent regions having a donut shape onto the SU-8 with photoinitiator (FIG. 6*b*). The UV-exposed portions 68 of the SU-8 were crosslinked (FIG. 6*c*). The SU-8 was then developed with propylene glycol methyl ether acetate (PGMEA) to remove the unexposed SU-8 (FIG. 6*d*), resulting in hollow cylindrical structures 68. These cylindrical structures 68 then were used to make a mold 70 from PDMS (FIG. 6*e*). This mold 70 was filled with polylactide (PLA) powder 72 which was then melted (FIG. 6*f*). After quenching, the polylactide needle array 74 was removed from the silicone mold (FIG. 6*g*). The process yielded hollow polylactide microneedles having non-tapered walls, an outer diameter of 100 microns, and a length of 300 microns.

EXAMPLE 4

Fabrication of Pointed Solid PLA Microneedles

Figure 7A:
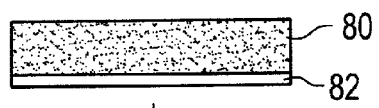
FIGS. 7*a-k* illustrate a process of fabricating solid polymeric microneedles having a tapered tip, shown in cross-section, using a combination of photolithography and micromolding.
Figure 7B:
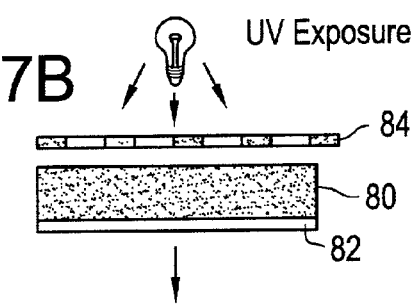
Figure 7C:
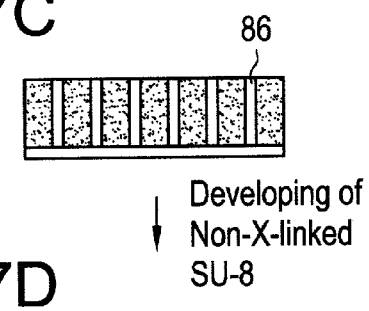
Figure 7D:
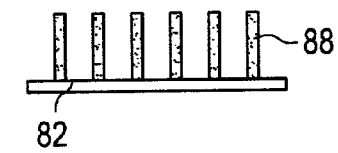
Figure 7E:
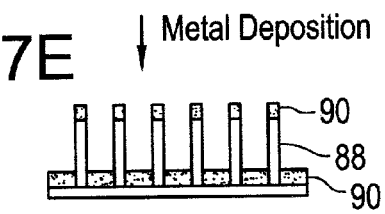
Figure 7F:
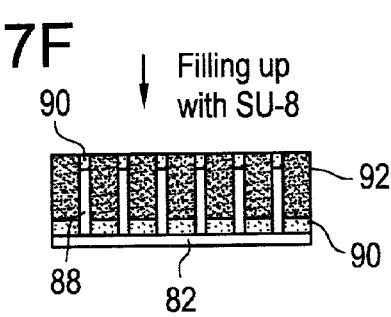
Figure 7L:
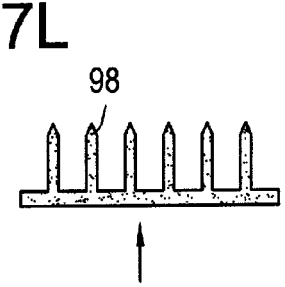
Figure 7J:
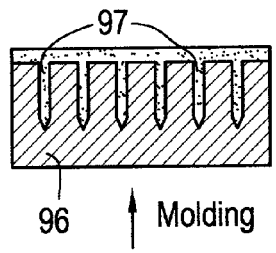
Figure 7I:
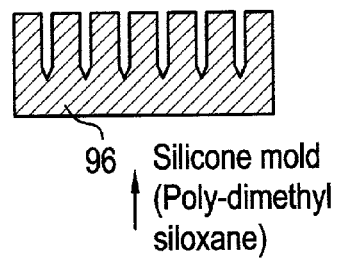
Figure 7H:
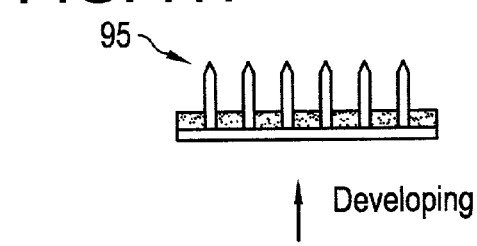
Figure 7G:
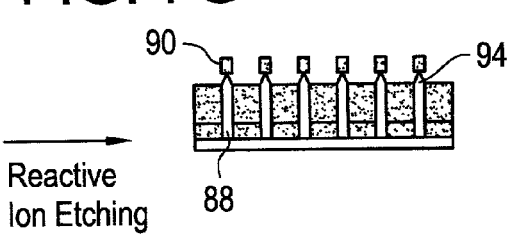

SU-8 epoxy photoresist (with photoinitiator) 80 was coated onto a silicon wafer substrate 82 (FIG. 7a). UV was then exposed through a dark optical mask 84 containing transparent regions having a donut shape onto the SU-8 with photo initiator (FIG. 7b). The UV-exposed portions 86 of the SU-8 were crosslinked (FIG. 7c). The SU-8 was then developed with propylene glycol methyl ether acetate (PGMEA) to remove the unexposed SU-8 (FIG. 7d). The resulting hollow cylindrical structures 88 were coated with metal 90 on the top surface of the cylindrical structure of crosslinked SU-8 by electron beam (E-Beam) metal deposition (FIG. 7e). This metal layer 90 serves a protective or shielding function during subsequent reactive ion etching. The metal could be chromium, titanium, or aluminum, for example. SU-8 without photo initiator 92 was then used to fill space between cylinders to protect them from side etching of the cylindrical structures 88 (FIG. 7f). To make sharp tips 94 on the cylindrical structures 88, the SU-8 epoxy was etched by reactive ion etching (RIE) (FIG. 7g) and developed again by PGMEA to remove SU-8 without photoinitiator (FIG. 7h). This resulted in cylindrical structures 88 (i.e. microneedles), made of crosslinked SU-8, having sharp tips 94 created during the reactive ion etching.

This microneedle structure 95 was used to make a mold 96 from PDMS (FIG. 7i), which can be used to make a replica structure, for example from a biodegradable material. The mold 96 was filled with a mixture 97 of 15% NaCl and 85% polymer solution (50% polylactic acid and 50% methylene chloride) (FIG. 7j). The polymeric material in the mold was then dried and melted under vacuuming to form polymeric microneedles and an integral substrate, which were then removed from the mold (FIG. 7k). The resulting microneedles 98 were 100 microns in diameter, along the shaft portion, and 400 microns long, with a sharp, tapered tip portion a few microns in length.

EXAMPLE 5

Fabrication of Solid Microneedles Having A Beveled Tip

Microneedle devices were made by microfabrication processes based on established methods (e.g., used to make integrated circuits, electronic packages and other microelectronic devices). SU-8 epoxy photoresist with photoinitiator 100 was coated onto a silicon wafer substrate 102 (FIG. 8a). Then UV (365 nm) was exposed through optical mask 103 transparent regions having circular shapes onto the SU-8 with a photoinitiator (FIG. 8b). The UV-exposed part 104 was crosslinked. The non-crosslinked SU-8 105 was then developed with PGMEA (propyl glycol methyl ether acetate).

Between the resulting cylindrical structures 104, a sacrificial thermoplastic polymer layer 106 was filled up to the height of cylindrical structures 104 (FIG. 8c). The polymer layer 106 was used to protect the cylindrical structures from side etching. The polymer layers 104 and 106 then were coated with a copper layer 108 by electron beam metal deposition (FIG. 8d). This copper layer 108 was etched by $H_2O/H_2SO_4/H_2O_2=10/1/1$ to make the desired pattern (FIG. 8e).

The pattern exposed only one side of the cylindrical structures 104. The exposed sacrificial polymer layer and cylindrical structures were then etched by RIE (FIG. 8f). Sacrificial polymer was removed by organic solvent, resulting in a structure 110 having SU-8 microneedles with beveled tips 111 (FIG. 8g).

Figure 10A:
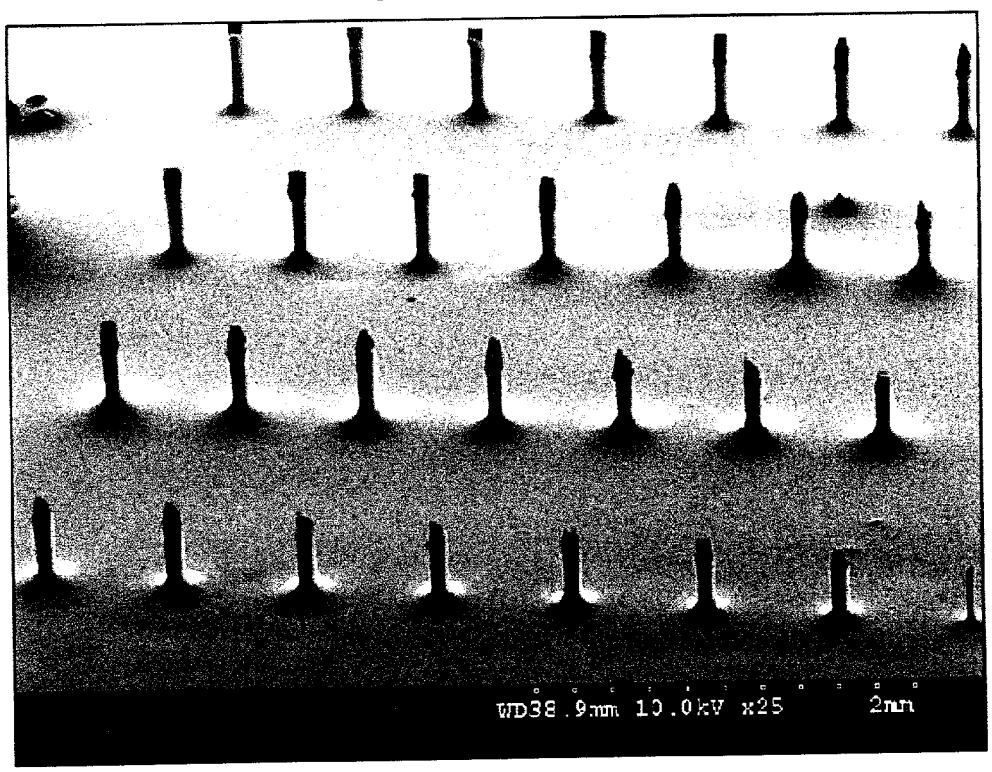
FIGS. 10*a-b* are micrographs of a solid polymeric microneedles having a beveled tip portion.
Figure 10B:
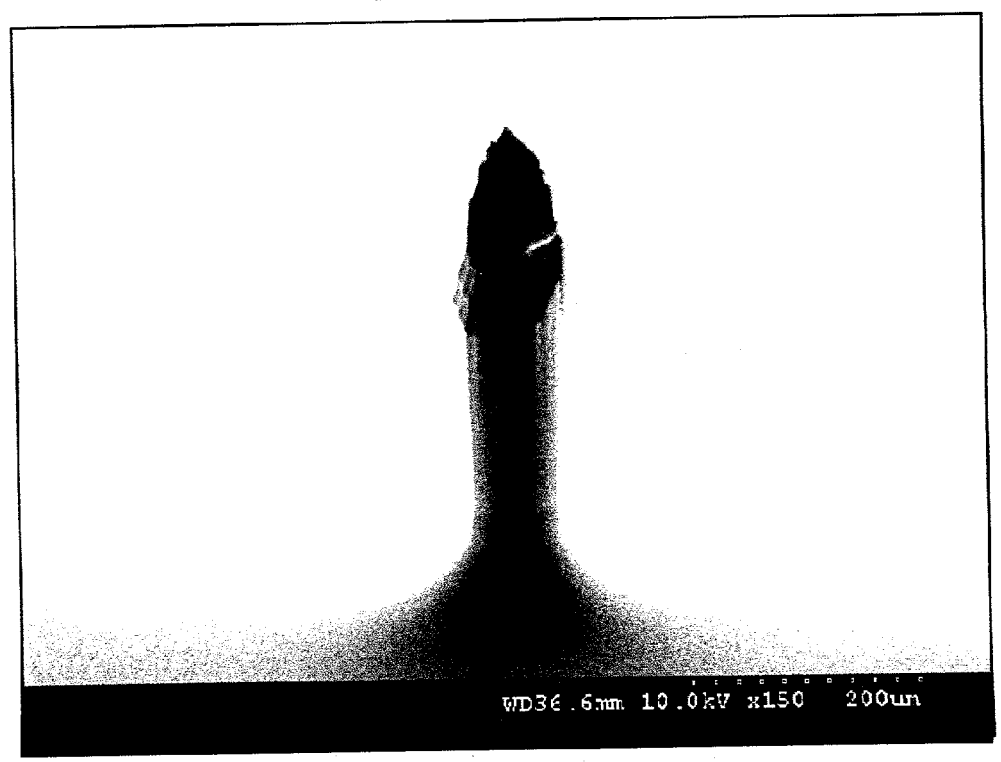

The structure 110 was then used to make a mold 112 of PDMS, which can be used to make a replica structure, for example from a biodegradable material. The silicone mold 112 was then filled with polyglycolide polymer powder 113 (FIG. 8h). The polymer powder was then melted under vacuum, thereby forming polymer microneedle structure 114 (FIG. 8i). FIG. 10a shows an array of these beveled microneedles, and FIG. 10b is a close-up photograph of an individual beveled microneedle.

EXAMPLE 6

Fabrication Of PGA Beveled Microneedles With Channels

Figure 9:
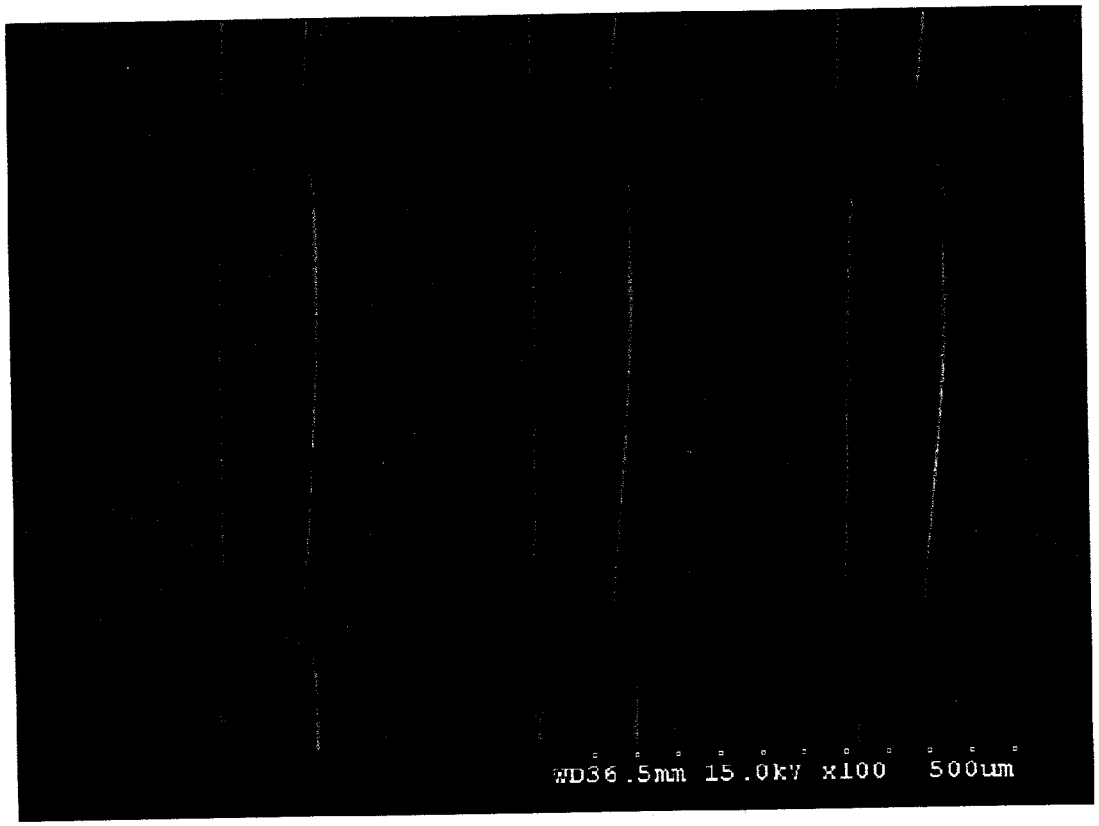
FIG. 9 is a micrograph of solid polymeric microneedles having a longitudinal channel.

SU-8 epoxy photoresist with photoinitiator was spin coated onto a silicon wafer. The coated wafer was exposed to UV (365 nm) through mask pattern having circular shape with square indention. The UV-exposed portion of the epoxy was crosslinked. The non-crosslinked portion of the epoxy was then developed with PGMEA. The square indention causes a longitudinal channel to be formed on the side of cylindrical structures. FIG. 9 shows an array of these microneedle structures having a longitudinal channel.

The resulting cylindrical structures with the channel were then filled with a sacrificial, thermoplastic polymer layer up to the height of cylindrical structure, under vacuum. Then, a copper layer was deposited by e-beam deposition onto the sacrificial polymer layer and cylindrical structures. This copper layer was then etched with a diluted sulfuric acid solution to make an etched pattern, as described in Example 5. Subsequently, the sacrificial polymer layer and cylindrical notch structures of crosslinked SU-8 was etched by RIE and the sacrificial polymer was removed using an organic solvent. The resulting beveled and notch microneedle structure then was used to make a silicone mold that can be used, as described in Example 5, to make a replica microneedle structures, for example from a biodegradable material.

EXAMPLE 7

Fabrication Of Beveled Microneedles Of PGA With A Protien

Carboxy methyl cellulose (CMC) and bovine serum albumin (BSA) were dissolved in water to make 4% CMC solution and 0.5% BSA with high viscosity. An array of polymeric beveled microneedles having an open longitudinal channel, made as described in the first part of Example 6, was placed into the CMC solution. A vacuum was then applied to fill the channels in the microneedles with CMC solution. The microneedles were then washed slightly with water to remove residual CMC outside of the channel. The microneedles were then allowed to dry. The process resulted in PGA microneedles having a channel filled with BSA in a CMC matrix. The BSA release rate would be controlled, in part, by the properties of the CMC.

EXAMPLE 8

Fabrication of Microneedles Having An Obelisk Shape

Figure 11A:
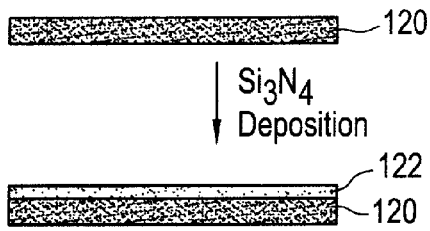
FIGS. 11*a-g* illustrate a process of fabricating solid polymeric microneedles having an obelisk shape, shown in cross-section, using a combination of photolithography and micromolding.
Figure 11B:
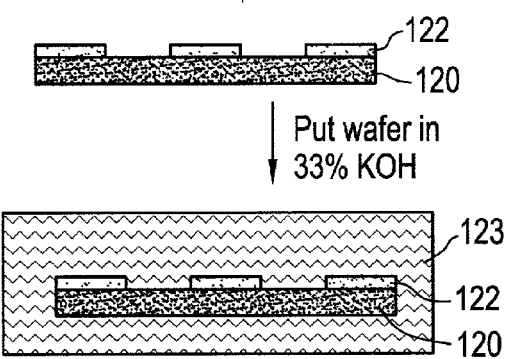

Silicon nitride was deposited onto a silicon wafer 120 to a thickness of 4000 Å by chemical vapor deposition (CVD), to make a hard mask for etching the silicon with KOH (FIG. 11a). The silicon nitride layer 122 was etched using reactive ion etching (RIE) with $SF_4+O_2$ chemistry. The silicon nitride was etched until the silicon was exposed, about 9.5 minutes (FIG. 11b). Then the photoresist was removed using RIE with $O_2$ chemistry, about 10 minutes. Alternatively, the photoresist was removed using warm acetone solvent, which is recommended because the acetone will not attack the silicon nitride.

Figure 4:
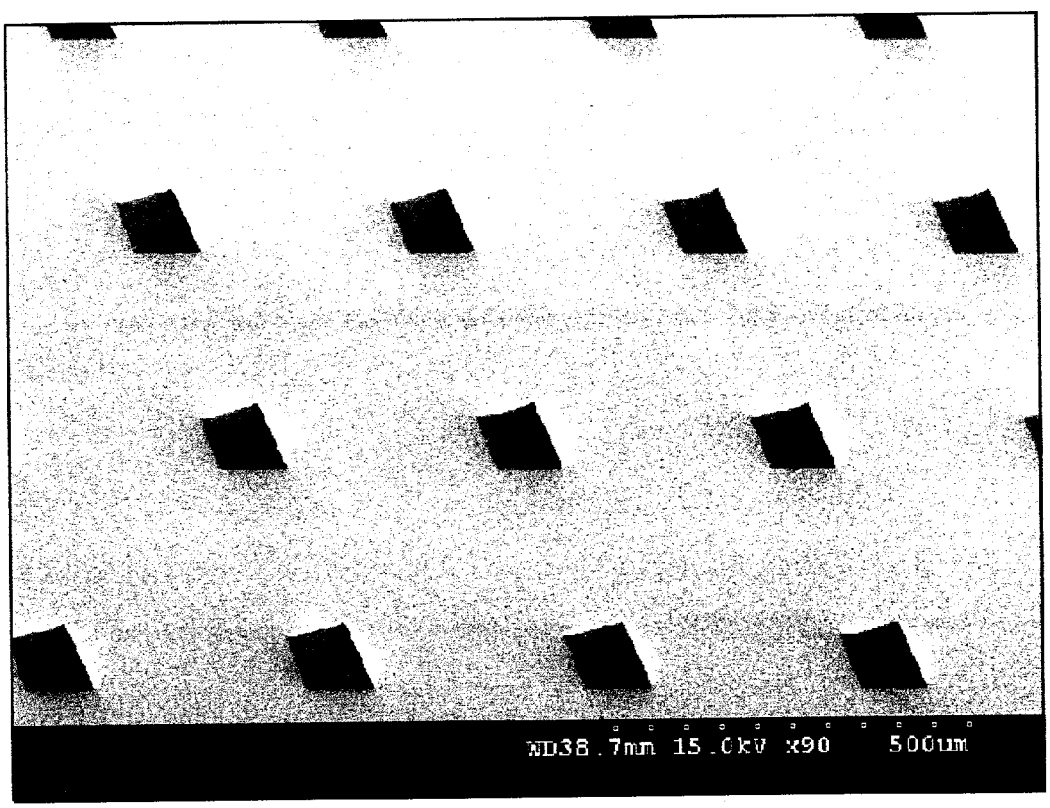
FIG. 4 is a micrograph of an interim structure in the fabrication process illustrated in FIG. 11*c*.
Figure 11C:
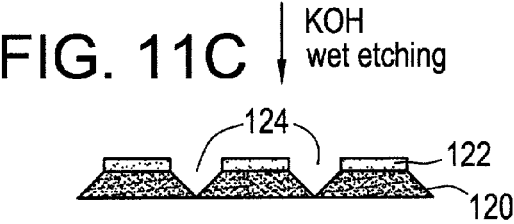
Figure 11D:
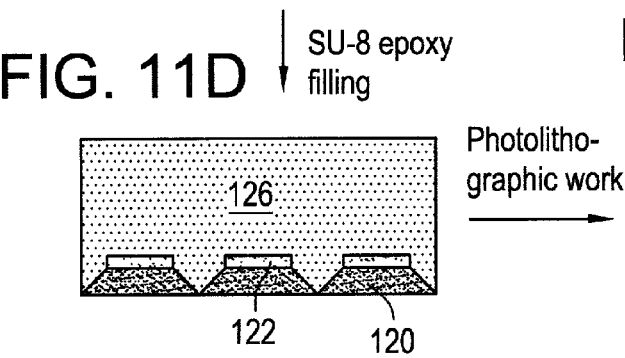
Figure 11G:
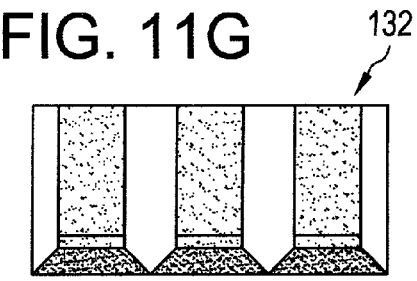
Figure 11F:
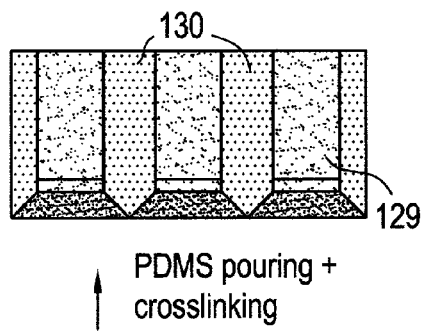
Figure 11E:
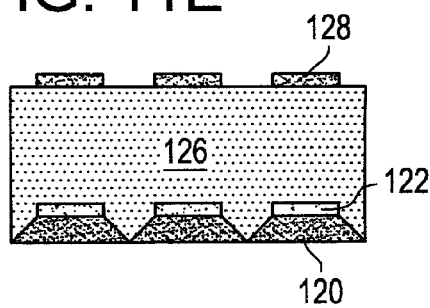
Figure 12:
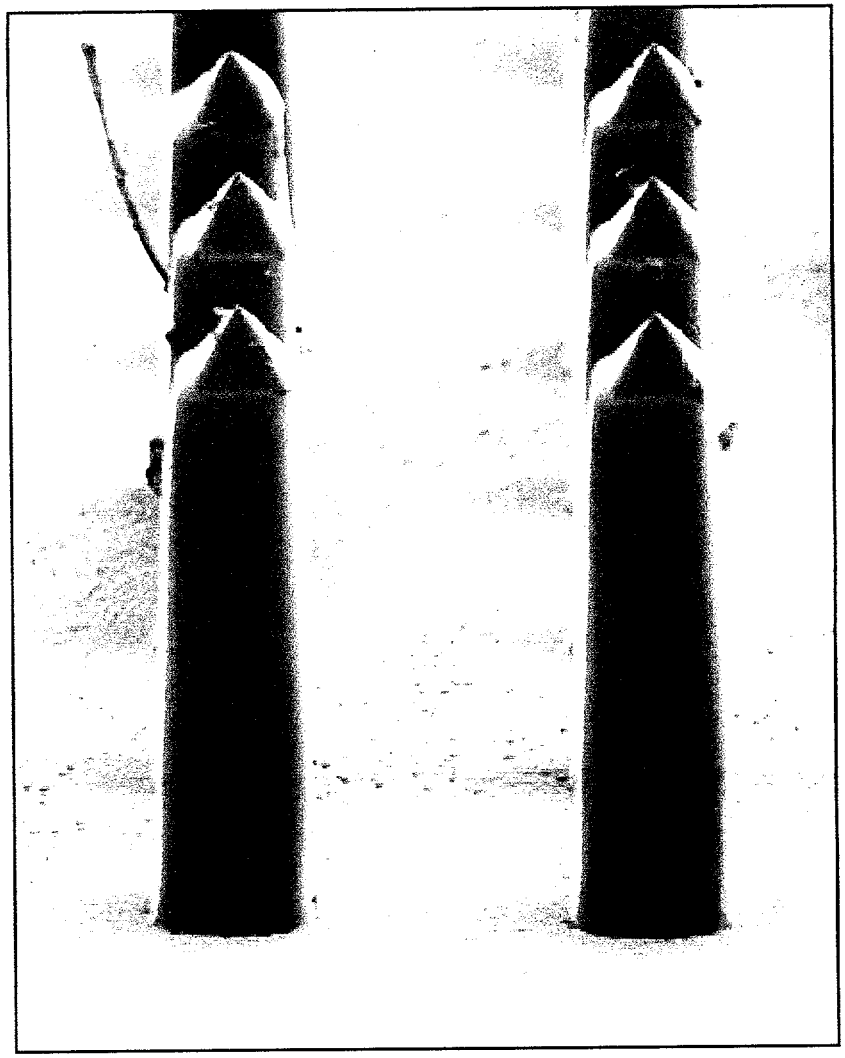
FIG. 12 is a micrograph of an array of solid polymeric microneedles having an obelisk shape.

Then the structure was placed into an etchant of KOH solution 123, which was heated to 75° C. Typical silicon etch rates for KOH are about 1.2 micron per minute, but this will vary with temperature and concentration. Silicon was etched to form pyramid structure holes 124 terminating in a sharp point (FIGS. 4 and 11c). Then, SU-8 epoxy photoresist with photoinitiator was coated 126 onto the etched structure (FIG. 11d). Subsequently, a second mask was aligned with the wafer, so that a second square pattern 128 could be transferred onto epoxy layer 126 in vertical alignment with silicon nitride patterns 122 (FIG. 11e). UV (365 nm) was exposed through optical mask transparent regions, crosslinking the exposed portions. The non-crosslinked epoxy was then developed with PGMEA, forming obelisk shaped structures 130. The spaces between the obelisk structures then were filled with PDMS 129 (FIG. 11f), and the cross linked SU-8 was then removed using RIE with $O_2$ chemistry, leaving only a PDMS mold 132 (FIG. 11g). Subsequently, polyurethane was poured into the PDMS mold and then crosslinked to form polymeric microneedles having an obelisk shape, as shown in FIG. 12.

A second identical PDMS mold was also made. It was then filled with polylactide or polyglycolide polymer powder. The polymer powder was melted under vacuum to fill the mold and form polymer microneedles. The polymer then was cooled, and the microneedles were removed from the mold.

EXAMPLE 9

Insertion And Removal Of Microneedles Into Skin In Vitro

Full thickness skin was obtained from human cadavers. The epidermis was separated from the dermis by immersion in 60° C. water for 2 minutes and then removed using a metal spatula. Isolated epidermis was rested onto a piece of tissue paper and polymeric microneedles fabricated by the methods described herein were inserted into the epidermis. The force required for insertion of the microneedles into the skin was less than that which can easily be applied by the experimenter's hand. Microneedles could be inserted and withdrawn multiple times without breaking. Microscopic observation showed holes formed in the skin by the microneedles.

EXAMPLE 10

Insertion And Removal Of Microneedles Into Skin In Vivo

Polymeric microneedles fabricated by the methods described herein were inserted into the skin of human volunteers. The force required for insertion of the microneedles into the skin was less than that which can easily be applied by the experimenter's hand. Microneedles could be inserted and withdrawn multiple times without breaking. Microneedles could be inserted into the skin under conditions for which the human subject did not report feeling pain.

EXAMPLE 11

Insertion And Breakage Of Microneedles Into Skin

Polymeric microneedles fabricated by the methods described herein were inserted into the skin using a force less than that which can easily be applied by the experimenter's hand. Then, a base of the microneedle array was moved vigorously in a direction parallel to the skin surface, thereby selectively breaking off microneedles from their substrate near to the base of the array. In this way, the array was separated and the individual microneedles remained embedded into the skin. The needles were left in the skin for some time and subsequently removed using forceps.

Publications cited herein and the material for which they are cited are specifically incorporated by reference. Nothing herein is to be construed as an admission that the invention is not entitled to antedate such disclosure by virtue of prior invention.

Modifications and variations of the methods and devices described herein will be obvious to those skilled in the art from the foregoing detailed description. Such modifications and variations are intended to come within the scope of the appended claims.

We claim:

1. A device for transport of molecules or energy across or into a biological barrier, comprising:
 a plurality of microneedles, wherein each microneedle formed of a first molding material, wherein the first molding material comprises a mixture of a) a polymer first material and b) a second material comprising rigid particles dispersed therein, wherein the first molding material is micromolded into the plurality of microneedles.

2. The device of claim 1, wherein the polymer is a biodegradable polymer.

3. The device of claim 2, wherein the polymer is selected from the group consisting of poly(lactide)s, poly(glycolide)s, poly(lactide-co-glycolide)s, polyanhydrides, polyorthoesters, polyetheresters, polycaprolactones, polyesteramides, poly(butyric acid)s, poly(valeric acid)s, polyhydroxyalkanoates, degradable polyurethanes, copolymers thereof, and blends thereof.

4. The device of claim 1, wherein the polymer is a non-biodegradable polymer.

5. The device of claim 1, where in the second material comprises a metal.

6. The device of claim 1, wherein the first molding material further comprises a drug.

7. The device of claim 2, wherein the molding material comprises a drug.

8. The device of claim 7, wherein the drug is a vaccine.

9. The device of claim 2, wherein the biodegradable polymer is a soluble polymer.

10. The device of claim 1, wherein the molding material comprises a salt or other leachable particle.

11. The device of claim 1, further comprising a substrate from which the plurality of microneedles extend.

12. The device of claim 1, wherein the microneedles have lengths between about 10 and 1000 microns.

13. The device of claim 12, wherein the microneedles have widths between about 10 and 500 microns.

14. The device of claim 1, wherein the second material undergoes a temperature sensitive phase change at human body temperature.

15. The device of claim 14, where in the second material is a hydrate.

16. The device of claim 1, wherein the first material and second material are disposed in a layered relationship with respect to each other.

17. The device of claim 16, wherein the first material and second material are disposed in an alternating horizontal layer configuration with respect to each other.

18. The device of claim 1 wherein the polymer first material is a porous material and the second material is filled into the voids or pores of the first material.

19. The device of claim 1 wherein the second material is a rapidly degradable polymer particle.

20. A device for transport of molecules or energy across or into a biological barrier, comprising;
    a plurality of microneedles, each microneedle formed of a polymer first material and a second material, wherein the second material comprises rigid particles that are dispersed throughout at least a portion of the polymer and wherein the first material and second material are disposed in a layered relationship with respect to each other, and wherein the first material and second material are disposed in an alternating horizontal layer configuration with respect to each other.

21. The device of claim 20, further comprising a substrate from which the plurality of microneedles extend.

22. The device of claim 20, wherein the polymer is a biodegradable polymer.

23. The device of claim 22, wherein the molding material comprises a drug.

24. The device of claim 22, wherein the biodegradable polymer is a soluble polymer.

25. The device of claim 20, wherein the molding material further comprises a drug.

26. The device of claim 20, wherein the second material comprises a vaccine.

27. A device for transport of molecules or energy across or into a biological barrier comprising;
    a plurality of microneedles, each microneedle formed of a first molding material, wherein the first molding material comprises a mixture of a) a polymer first material and b) a second material, comprising rigid particles dispersed therein; and
    a substrate from which the plurality of microneedles extend.

28. The device of claim 27, wherein the polymer first material is a biodegradable polymer.

29. The device of claim 28, wherein the molding material comprises a drug.

30. The device of claim 28, wherein the biodegradable polymer is a soluble polymer.

31. The device of claim 27, wherein the molding material further comprises a drug.

32. The device of claim 27, wherein the second material undergoes a temperature sensitive phase change at human body temperature.

33. The device of claim 32, wherein the second material is a hydrate.

34. The device of claim 27, wherein the first material and second material are disposed in a layered relationship with respect to each other.

35. The device of claim 34, wherein the first material and second material are disposed in an alternating horizontal layer configuration with respect to each other.

36. The device of claim 27, wherein the second material comprises a vaccine.

\* \* \* \* \*